US010870099B2

(12) United States Patent
Fan et al.

(10) Patent No.: US 10,870,099 B2
(45) Date of Patent: Dec. 22, 2020

(54) COMPOSITIONS AND METHODS FOR THE AMPLIFICATION OF NUCLEIC ACIDS

(71) Applicant: Illumina, Inc., San Diego, CA (US)

(72) Inventors: Jian-Bing Fan, San Diego, CA (US); Kevin L. Gunderson, Encinitas, CA (US); Frank J. Steemers, Encinitas, CA (US); Dmitry K. Pokholok, San Marcos, CA (US); Fiona Kaper, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 629 days.

(21) Appl. No.: 14/416,563

(22) PCT Filed: Feb. 21, 2013

(86) PCT No.: PCT/US2013/027017
§ 371 (c)(1),
(2) Date: Jan. 22, 2015

(87) PCT Pub. No.: WO2014/018093
PCT Pub. Date: Jan. 30, 2014

(65) Prior Publication Data
US 2015/0360193 A1 Dec. 17, 2015

Related U.S. Application Data

(60) Provisional application No. 61/676,153, filed on Jul. 26, 2012.

(51) Int. Cl.
*B01J 19/00* (2006.01)
*C12Q 1/6844* (2018.01)

(52) U.S. Cl.
CPC ........ *B01J 19/0046* (2013.01); *C12Q 1/6844* (2013.01); *B01J 2219/00585* (2013.01); *B01J 2219/00722* (2013.01)

(58) Field of Classification Search
CPC .......... C12Q 1/6844; B01J 2219/00585; B01J 2219/00722; B01J 19/0046
See application file for complete search history.

(56) References Cited

U.S. PATENT DOCUMENTS

| 4,469,863 | A | 9/1984 | Ts'o |
| 5,001,050 | A | 3/1991 | Blanco |
| 5,034,506 | A | 7/1991 | Summerton |
| 5,043,272 | A | 8/1991 | Hartley |
| 5,130,238 | A | 7/1992 | Malek |
| 5,198,543 | A | 3/1993 | Blanco |
| 5,216,141 | A | 6/1993 | Benner |
| 5,235,033 | A | 8/1993 | Summerton |
| 5,386,023 | A | 1/1995 | Sanghvi |
| 5,455,166 | A | 10/1995 | Walker |
| 5,602,240 | A | 2/1997 | De Mesmaeker |
| 5,637,684 | A | 6/1997 | Cook |
| 5,644,048 | A | 7/1997 | Yau |
| 5,681,702 | A | 10/1997 | Collins |
| 6,214,587 | B1 | 4/2001 | Dattagupta |
| 6,306,588 | B1 | 10/2001 | Solus |
| 6,365,375 | B1 | 4/2002 | Dietmaier et al. |
| 7,670,810 | B2 | 3/2010 | Gunderson |
| 2003/0096986 | A1 | 5/2003 | Mei |
| 2004/0014105 | A1* | 1/2004 | Schroeder ............ C07H 21/04 435/6.12 |
| 2004/0180361 | A1* | 9/2004 | Dahl ................. C12N 15/1096 435/6.1 |
| 2004/0259100 | A1* | 12/2004 | Gunderson .......... C12Q 1/6827 435/6.11 |
| 2010/0184152 | A1* | 7/2010 | Sandler ................ C12Q 1/6846 435/91.2 |
| 2011/0195457 | A1* | 8/2011 | Nelson ................... C12P 19/34 435/91.2 |
| 2013/0210078 | A1 | 8/2013 | Nelson et al. |

FOREIGN PATENT DOCUMENTS

| EP | 2064332 | 6/2009 |
| EP | 2261371 | 12/2010 |
| EP | 2264188 | 12/2010 |
| WO | 02/101022 | 12/2002 |
| WO | 2004/081225 | 9/2004 |
| WO | 2006/020617 | 2/2006 |
| WO | 2009/105531 | 8/2009 |
| WO | WO/2009135093 | 11/2009 |
| WO | 2011/131192 | 10/2011 |

OTHER PUBLICATIONS

Robinson et al. (2004) "Simple sequence repeat marker loci discovery using SSR primer" Bioinformatics 20(9):1475-1476.*
Hosono, et al., "Unbiased whole-genome amplification directly from clinical samples", Genome Research, 13(5), 2003, 954-964.
Hughes, S. et al., "The use of whole genome amplification in the study of human disease", Progress in Biophysics & Molecular Biology 88, 2005, 173-189.
Ausubel et al., Current Protocols in Molecular Biology, Table of Contents, eds John Wiley & Sons, Inc. (1998).
Beaucage et al., The Functionalization of Oligonucleotides Via Phosphoramidite Derivatives, Tetrahedron 49(10):1925 (1993).
Brill et al., Synthesis of oligodeoxynucleoside phosphorodithioates via thioamidites, J. Am. Chem. Soc. 11 1:2321 (1989).
Carlsson et al., Screening for genetic mutations, Nature 380:207 (1996).
Casas et al., Evaluation of Different Amplification Protocols for Use in Primer-Extension Preamplification Biotechniques 20:219-25 (1996).
Cheung et al., Whole genome amplification using a degenerate oligonucleotide primer allows hundreds of genotypes to be performed on less than one nanogram of genomic DNA, Proc. Natl. Acad. Sci. USA, 93:14676-79 (1996).

(Continued)

*Primary Examiner* — Robert H Havlin
(74) *Attorney, Agent, or Firm* — Knobbe, Martens, Olson & Bear LLP

(57) ABSTRACT

The present disclosure relates to systems and methods for the amplification of nucleic acids, including, but not limited to, the amplification of nucleic acid libraries and whole genome amplification.

18 Claims, 7 Drawing Sheets

Specification includes a Sequence Listing.

(56) References Cited

OTHER PUBLICATIONS

Dean et al., Comprehensive human genome amplification using multiple displacement amplification, Proc Natl. Acad. Sci USA 99:5261-66 (2002).
Dempcy et al., Synthesis of a thymidyl pentamer of deoxyribonucleic guanidine and binding studies with DNA homopolynucleotides, Proc. Natl. Acad. Sci. USA 92:6097 (1995).
Egholm, et al, PNA hybridizes to complementary oligonucleotides obeying the WatsonCrick hydrogen-bonding rules, Nature, 365:566 (1993).
Egholm, Peptide nucleic acids (PNA). Oligonucleotide analogs with an achiral peptide backbone J. Am. Chem. Soc. 114:1895 (1992).
Extended Search Report and Opinion dated Oct. 9, 2018 in Application No. 18183934.1.
Grothues et al. PCR amplification of megabase DNA with tagged random primers (T-PCR), Nucleic Acids Res. 21(5):1321-2 (1993).
Horn, et al, Oligonucleotides with alternating anionic and cationic phosphoramidate linkages: Synthesis and hybridization of stereo-uniform isomers, Tetrahedron Lett. 37(6):743 (1996).
Jenkins et al., The biosynthesis of carbocyclic nucleosides, Chem. Soc. Rev. 3:169-176 (1995).
Jung et al., Bacteriophage PRD1 DNA polymerase: Evolution of DNA polymerases, Proc. Natl. Acad. Sci. USA 84:8287 (1987).
Jung et al., Hybridization of Alternating Cationic/Anionic Oligonucleotides to RNA Segments, Nucleoside & Nucleotide 13:1597 (1994).
Kiedrowshi et al., Parabolic growth of a self-replicating hexadeoxynucleotide bearing a 3'-5'-phosphoamidate linkage, Angew. Chem. Intl. Ed. English 30:423 (1991).
Kittler et al., A whole genome amplification method to generate long fragments from low quantities of genomic DNA, Anal. Biochem. 300:237-44 (2002).
Kong et al., Characterization of a DNA polymerase from the hyperthermophile archaea Thermococcus litoralis, J. Biol. Chem. 268.1965-1975 (1993).
Kutyavin et al. Oligonucleotides Containing 2-Aminoadenine and 2-Thiothymine Act as Selectively Binding Complementary Agents, Biochemistry, 35:11170-11176 (1996).
Lage et al., Whole genome analysis of genetic alterations in small DNA samples using hyperbranched strand displacement amplification and array—CGH, Genome Research 13:294-307 (2003).
Letsinger et al., Cationic oligonucleotides, J. Am. Chem. Soc. 110:4470 (1988).
Letsinger et al., Effects of pendant groups at phosphorus on binding of d-ApA analogues, Nucl. Acids Res. 14:3487 (1986).
Letsinger, Phosporamidate analogs of oligonucleotides, J. Org. Chem. 35:3800 (1970).
Mag et al., Synthesis and selective cleavage of an oliodeoxynucleotide containing a bridged internucleotide 5'-phosphorothioate linkage, Nucleic Acids Res. 19:1437 (1991).
Matsumoto et al., Primary structure of bacteriophage M2 DNA polymerase: conserved segments within protein-priming DNA polyumerases and DNA polymerase I of *Escherichia coli*, Gene 84:247 (1989).
Meier et al., Peptide nucleic acids (PNAs)—Unusual properties of nonionic oligonucleotide analogues, Chem. Int. Ed. Engl. 31:1008 (1992).
Mesmaeker et al., Comparison of rigid and flexible backbones in antisense oligonucleotides, Bioorganic & Medicinal Chem. Left. 4:395 (1994).
Olsen, et al., PCR-DHPLC assay for the identification of predator-prey interactions, Journal of Plankton Research 34(4):277-285 (2012).
Pauwels et al., Biological activity of new 2-5A analogues, Chemica Scripta 26:141 (1986).
Rawls, Optimistic about antisense: promising clinical results and chemical strategies for further improvements delight antisense drug researchers, C & E News Jun. 2, 1997 p. 35.
Sambrook et al., Molecular Cloning: A Laboratory Manual, Cold Spring Harbor Laboratory Press, Cold Spring Harbor, New York (2001) (table of contents only).
Sawai et al, Synthesis and properties of oligoadenylic acids containing 2'-5' phosphoramide linkage, Chem. Lett. 805 (1984).
Singer et al., Libraries for genomic SELEX, Nucl. Acid. Res. 25(4):781-786 (1997).
Sprinzl et al., Enzymatic incorporation of ATP and CTP analogues into the 3' end of tRNA, Eur. J. Biochem. 81:579 (1977).
Vieria, et al., Miscrosatellite markers : what they mean and why they are so useful. Genetics and Molecular Biology, 39(3) :312-328 (2016).
Walker and Linn, Detection of *Mycobacterium tuberculosis* DNA with thermophilic strand displacement amplification and fluorescence polarization, Clinical Chemistry 42:1604-1608 (1996).
Walker et al., Molecular Methods for Virus Detection, Academic Press, Inc., 1995 (table of contents).
Walker et al., Strand displacement amplification—an isothermal, in vitro DNA amplification technique, Nucl. Acids Res. 20:1691-96 (1992).
Yang et al., Mutant *Thermotoga neapolitana* DNA polymerase I: altered catalytic properties for non-tempted nucleotide addition and incorporation of correct nucleotides, Nucl. Acids Res. 30:4314-4320 (2002).

\* cited by examiner

SEQUENCE LISTING

<160> NUMBER OF SEQ ID NOS: 5

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcgcgagtta a                                                          11

```
<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
attgcgaacg a                                                            11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttaactcgcg a                                                            11

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcgttcgcaa t                                                            11

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(31)
<223> OTHER INFORMATION: a, c, t, g, unknown or other

<400> SEQUENCE: 5
tcgcgagtta aattgcgaac gannnnnnnn n                                      31
```

COMPOSITIONS AND METHODS FOR THE AMPLIFICATION OF NUCLEIC ACIDS

RELATED APPLICATIONS

This application is the U.S. National Phase of Int. App. No. PCT/US2013/027017 filed on Feb. 21, 2013 which was published in English as WO 2014/018093 on Jan. 30, 2014 and claims priority to U.S. Provisional Application No. 61/676,153, filed on Jul. 26, 2012, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jul. 20, 2015, is named IP-0611-US_SL.txt and is 1,662 bytes in size.

FIELD OF THE INVENTION

The present disclosure relates generally to the fields of genetics and medicine. More specifically, the present disclosure relates to the amplification of nucleic acid libraries, including whole genomes.

BACKGROUND

High throughput genotyping applications rely on efficient and relatively unbiased amplification, such as whole genome amplification (WGA), of genomic DNA. Random primer amplification and multiple displacement amplification (MDA) can be used in a large number of different applications from amplifying DNA to creating genomic sequencing libraries. However, such methods can result in biased amplification which can result in a biased data set. The ability to amplify target DNA in a relatively unbiased manner is important in many applications, particularly in sequencing. However, there remains a great need for amplification methodologies which result in improved unbiased amplification of target nucleic acid libraries.

SUMMARY OF THE INVENTION

Presented herein are methods, compositions and kits for the amplification of nucleic acid samples to generate nucleic acid libraries. The methods, compositions and kits presented herein are surprisingly effective in reducing bias that occurs when amplifying a nucleic acid sample using random primers.

Accordingly, presented herein is a method of creating a nucleic acid library from a nucleic acid sample, the method comprising: a) providing a set of amplification primers to a nucleic acid sample, the set of amplification primers comprising a plurality of random primers and a plurality of locus specific primers, wherein the locus specific primers are configured to amplify a plurality of predetermined regions of the nucleic acid library, and wherein the random primers are in greater abundance compared to the locus specific primers; and b) amplifying the nucleic acid library using the set of amplification primers, thereby creating a nucleic acid library.

In some aspects of the above-described method, the set of amplification primers can be a mixture of primers. In certain aspects, the random primers are from approximately 5 to approximately 18 nucleotides in length. In certain other aspects, the random primers are 9 nucleotides in length. In some aspects, the locus specific primers can be of equal length to the random primers. In other aspects, the locus specific primers can be shorter than the random primers. In still other aspects, the locus specific primers can be longer than the random primers. In some aspects, the locus specific primers are configured to block or reduce amplification of one or more predetermined regions of the nucleic acid library. In some aspects, the locus specific primers comprise a 3' block or lack a 3' OH group.

In some aspects of the above-described method, the nucleic acid sample comprises a genomic DNA. In certain aspects, the genomic DNA comprises human DNA. In certain other aspects, the nucleic acid sample comprises a plurality of genomic DNAs. In still other aspects, the nucleic acid sample comprises DNA from one or more economically important species. In some aspects, the nucleic acid sample comprises DNA from one or more plants, fungi, protists, bacteria and/or archaebacteria. In some aspects, the nucleic acid sample comprises nucleic acids other than DNA. In certain aspects, the nucleic acid sample comprises DNA from cellular organelles, such as mitochondrial DNA, chloroplastic DNA and/or DNA from other cellular organelles.

In some aspects of the above-described method the random amplification primers comprise one or more quasi-random primers that are selected from the group consisting of an AT-rich set of random amplification primers; a set of random amplification primers comprising AT-rich 5' termini; a set of variable-length random amplification primers, wherein each primer comprises a random 3' portion and a degenerate 5' terminus, the degenerate 5' terminus of which can be proportional in length to the A/T content of the random 3' portion of the primer; a set of Tm-normalized amplification primers, wherein each primer of the set comprises one or more base analogues that can normalize the Tm of each primer to the Tm of other primers in the set of primers; a set of random amplification primers, wherein each primer comprises a random 3' portion and a constant 5' priming portion; a set of random amplification primers, wherein each primer comprises a random 3' portion and a constant 5' priming portion, and wherein the random 3' portion comprises RNA; a set of random amplification primers, wherein each primer comprises a random 3' portion and a constant 5' priming portion, and wherein the random 3' portion comprises at least one non-natural base selected from the group consisting of nucleic acids including 2'-deoxy-2-thiothymidine (2-thio-dT), 2-aminopurine-2'-deoxyriboside (2-amino-dA), N4-ethyl-2'-deoxycytidine (N4-Et-dC), N4-methyl deoxycytidine (N4-Me-dC), 2'-deoxyinosine, 7-deazaguanine (7-deaza-G), 7-iodo-7-deazaguanine (I-deazaG), 7-methyl-7-deazaguanine, (MecG), 7-ethyl-7-deazaguanine (EtcG) and any combination of the foregoing sets of primers. The quasi-random primers set forth above are described in further detail herein. In some embodiments described herein, the quasi-random primers are provided in pairs or sets.

Also presented herein is a kit for amplifying a nucleic acid sample, wherein the kit comprises a plurality of random primers and a plurality of locus specific primers configured to amplify a plurality of predetermined regions of a nucleic acid library. In certain aspects, the kit further comprises a set of instructions for using the random primers and the locus specific primers in an amplification reaction set, wherein the random primers are in greater abundance compared to the locus specific primers. In certain aspects, the kit further comprises a set of instructions for combining the set of amplification primers with a nucleic acid library and amplifying the nucleic acid library.

In some aspects of the amplification kit described herein, the kit further comprises a DNA polymerase. In certain aspects, the random primers can be from approximately 5 to 18 nucleotides in length. In certain other aspects, the random primers are 9 nucleotides in length. In some aspects, the locus specific primers can be of equal length to the random primers. In other aspects, the locus specific primers can be shorter than the random primers. In still other aspects, the locus specific primers can be longer than the random primers.

In addition to the foregoing method, also presented herein is a method of creating a nucleic acid library from a nucleic acid sample, the method comprising: a) amplifying a nucleic acid sample with an AT-rich set of random amplification primers. In certain aspects, the AT-rich set of random amplification primers is a mixture of primers.

In some aspects, of the above-described method the nucleic acid sample comprises a genomic DNA. In certain other aspects, the nucleic acid sample comprises a plurality of genomic DNAs. In still other aspects, the nucleic acid sample comprises DNA from one or more economically important species. In some aspects, the nucleic acid sample comprises DNA from one or more plants, fungi, protists, bacteria and/or archaebacteria. In some aspects, the nucleic acid sample comprises nucleic acids other than DNA. In certain aspects, the nucleic acid sample comprises mitochondrial DNA, chloroplastic DNA and/or DNA from other cellular organelles.

In some aspects of the above-described method, the overall composition of the AT-rich set of random amplification primers is greater than 25% A and 25% T. In certain aspects, the AT-rich set of random amplification primers comprises 30% A, 20% C, 20% G, and 30% T. In certain other aspects, the AT-rich set of random amplification primers comprises 35% A, 15% C, 15% G, and 35% T. In still other aspects, the AT-rich set of random amplification primers are from 5 to 18 nucleotides in length.

Also presented herein is a kit for amplifying a nucleic acid sample, wherein the kit comprises an AT-rich set of random amplification primers. In certain aspects, the kit further comprises a set of instructions for combining the set of amplification primers with a nucleic acid library and amplifying the nucleic acid library. In certain other aspects, the kit further comprises a DNA polymerase. In still other aspects, the AT-rich set of random amplification primers is a mixture of primers.

Also presented herein is a method of creating a nucleic acid library from a nucleic acid sample, the method comprising: a) amplifying a nucleic acid sample with a set of random amplification primers, the random amplification primers comprising AT-rich 5' tails. In certain aspects, the set of random amplification primers is a mixture of primers.

In some aspects of the above-described method the nucleic acid sample comprises a genomic DNA. In certain other aspects, the nucleic acid sample comprises a plurality of genomic DNAs. In still other aspects, the nucleic acid sample comprises DNA from one or more economically important species. In some aspects, the nucleic acid sample comprises DNA from one or more plants, fungi, protists, bacteria and/or archaebacteria. In some aspects, the nucleic acid sample comprises nucleic acids other than DNA. In certain aspects, the nucleic acid sample comprises nucleic acids from cellular organelles such as mitochondrial DNA, chloroplastic DNA and/or DNA from other cellular organelles.

In some aspects of the above-described method, the AT-rich 5'tail comprises 30% A, 20% C, 20% G, and 30% T. In certain aspects, the AT-rich 5'tail comprises 35% A, 15% C, 15% G, and 35% T. In certain other aspects, the AT-rich 5'tail comprises 40% A, 10% C, 10% G, and 40% T. In still other aspects, the AT-rich 5'tail comprises 50% A and 50% T.

Also presented herein is a kit for amplifying a nucleic acid sample, wherein the kit comprises a set of random amplification primers, the random amplification primers comprising AT-rich 5' tails. In certain aspects, the kit further comprises a set of instructions for combining the set of amplification primers with a nucleic acid library and amplifying the nucleic acid library. In certain other aspects, the kit further comprises a DNA polymerase. In still other aspects, the set of random amplification primers is a mixture of primers.

Also presented herein is a method of creating a nucleic acid library from a nucleic acid sample, the method comprising: amplifying a nucleic acid sample with a set of variable-length random amplification primers, wherein each variable-length random amplification primer comprises a random 3' portion and a degenerate 5' tail, the degenerate 5' tail being proportional in length to the A/T content of the random 3' portion of the primer. In certain aspects, the set of variable-length random amplification primers is a mixture of primers.

In some aspects, of the above-described method the nucleic acid sample comprises a genomic DNA. In certain other aspects, the nucleic acid sample comprises a plurality of genomic DNAs. In still other aspects, the nucleic acid sample comprises DNA from one or more economically important species. In some aspects, the nucleic acid sample comprises DNA from one or more plants, fungi, protists, bacteria and/or archaebacteria. In some aspects, the nucleic acid sample comprises nucleic acids other than DNA. In certain aspects, the nucleic acid sample comprises mitochondrial DNA, chloroplastic DNA and/or DNA from other cellular organelles.

In certain aspects of the above-described method, the 5' tail of the variable-length random amplification primer comprises at least one degenerate nucleotide for every two A or T nucleotides in the random 3' portion.

Also presented herein is a kit for amplifying a nucleic acid sample, wherein the kit comprises a set of variable-length random amplification primers, wherein each variable-length random amplification primer comprises a random 3' portion and a degenerate 5' tail, the degenerate 5' tail being proportional in length to the A/T content of the random 3' portion of the primer. In certain aspects, the kit further comprises a set of instructions for combining the set of amplification primers with a nucleic acid library and amplifying the nucleic acid library. In certain other aspects, the kit further comprises a DNA polymerase. In still other aspects, the set of variable-length random amplification primers is a mixture of primers.

Also presented herein is a method of creating a nucleic acid library from a nucleic acid sample, the method comprising: amplifying a nucleic acid sample with a set of Tm-normalized amplification primers, wherein each primer of the set of Tm-normalized amplification primers comprises one or more base analogues that normalize the Tm of each primer to the Tm of other primers in the set of primers. In certain aspects, the set of Tm-normalized amplification primers is a mixture of primers.

In some aspects, of the above-described method the nucleic acid sample comprises a genomic DNA. In certain other aspects, the nucleic acid sample comprises a plurality of genomic DNAs. In still other aspects, the nucleic acid sample comprises DNA from one or more economically important species. In some aspects, the nucleic acid sample comprises DNA from one or more plants, fungi, protists, bacteria and/or archaebacteria. In some aspects, the nucleic acid sample comprises nucleic acids other than DNA. In certain aspects, the nucleic acid sample comprises mitochondrial DNA, chloroplastic DNA and/or DNA from other cellular organelles.

In certain aspects of the above-described method, the one or more base analogues are selected from the group consisting of 2-thio-dT, 2-amino-dA, N4-Et-dC, and 7-deaza-G.

Also presented herein is a kit for amplifying a nucleic acid sample, wherein the kit comprises a set of Tm-normalized amplification primers, wherein each primer of the set of Tm-normalized amplification primers comprises one or more base analogues that normalize the Tm of each primer to the Tm of other amplification primers in the kit. In certain aspects, the kit further comprises a set of instructions for combining the set of amplification primers with a nucleic acid library and amplifying the nucleic acid library. In certain other aspects, the kit further comprises a DNA polymerase. In still other aspects, the set of Tm-normalized amplification primers is a mixture of primers.

Also presented herein is a method of creating a nucleic acid library from a nucleic acid sample, the method comprising: a) amplifying a nucleic acid sample with a set of random amplification primers, wherein each primer comprises a random 3' portion and a constant 5' priming portion, thereby producing amplification products, wherein each amplification product comprises the constant 5' priming portion; b) circularizing the amplification products; and c) amplifying the circularized amplification products using primers which hybridize to the constant 5' priming portion. In certain aspects, the amplifying in step (c) comprises performing multiple displacement amplification. In certain aspects, the set of random amplification primers is a mixture of primers.

In some aspects, of the above-described method the nucleic acid sample comprises a genomic DNA. In certain other aspects, the nucleic acid sample comprises a plurality of genomic DNAs. In still other aspects, the nucleic acid sample comprises DNA from one or more economically important species. In some aspects, the nucleic acid sample comprises DNA from one or more plants, fungi, protists bacteria and/or archaebacteria. In some aspects, the nucleic acid sample comprises nucleic acids other than DNA. In certain aspects, the nucleic acid sample comprises mitochondrial DNA, chloroplastic DNA and/or DNA from other cellular organelles.

In certain aspects of the above-described method, the amplification primers comprise at least one non-natural base between the random 3' portion and the constant 5' priming portion. In certain aspects, the non-natural base is isoC.

Also presented herein is a kit for amplifying a nucleic acid sample, wherein the kit comprises a set of random amplification primers comprising a random 3' portion and a constant 5' priming portion. In certain aspects, the kit further comprises a set of instructions for combining the set of amplification primers with a nucleic acid library and amplifying the nucleic acid library. In certain other aspects, the kit further comprises a DNA polymerase. In still other aspects, the set of random amplification primers is a mixture of primers.

Also presented herein is a method of creating a nucleic acid library from a nucleic acid sample, the method comprising: a) amplifying a nucleic acid sample with a set of random amplification primers, wherein each primer comprises a random 3' portion and a constant 5' priming portion, and wherein the random 3' portion comprises RNA, thereby producing amplification products, wherein each amplification product comprises the constant 5' priming portion. In certain aspects, the set of random amplification primers is a mixture of primers.

In some aspects, of the above-described method the nucleic acid sample comprises a genomic DNA. In certain other aspects, the nucleic acid sample comprises a plurality of genomic DNAs. In still other aspects, the nucleic acid sample comprises DNA from one or more economically important species. In some aspects, the nucleic acid sample comprises DNA from one or more plants, fungi, protists bacteria and/or archaebacteria. In some aspects, the nucleic acid sample comprises nucleic acids other than DNA. In certain aspects, the nucleic acid sample comprises mitochondrial DNA, chloroplastic DNA and/or DNA from other cellular organelles.

In certain aspects the above-described method further comprises: b) circularizing the amplification products; and c) amplifying the circularized amplification products using primers which hybridize to the constant 5' priming portion. In certain aspects, the amplifying in step c) comprises performing multiple displacement amplification.

Also presented herein is a kit for amplifying a nucleic acid sample, wherein the kit comprises a set of random amplification primers, the primers comprising a random 3' portion and a constant 5' priming portion, wherein the random 3' portion comprises RNA. In certain aspects, the kit further comprises a set of instructions for combining the set of amplification primers with a nucleic acid library and amplifying the nucleic acid library. In certain other aspects, the kit further comprises a DNA polymerase. In still other aspects, the set of random amplification primers is a mixture of primers.

Also presented herein is a method of creating a nucleic acid library from a nucleic acid sample, the method comprising: amplifying a nucleic acid sample with a set of random amplification primers, wherein each primer of the set comprises a random 3' portion and a constant 5' priming portion, and wherein the random 3' portion comprises at least one non-natural base selected from the group consisting of: 2-thio-dT and 2-amino-dA, thereby producing amplification products, wherein each amplification product comprises the constant 5' priming portion. In certain aspects, the set of random amplification primers is a mixture of primers.

In some aspects, of the above-described method the nucleic acid sample comprises a genomic DNA. In certain other aspects, the nucleic acid sample comprises a plurality of genomic DNAs. In still other aspects, the nucleic acid sample comprises DNA from one or more economically important species. In some aspects, the nucleic acid sample comprises DNA from one or more plants, fungi, protists bacteria and/or archaebacteria. In some aspects, the nucleic acid sample comprises nucleic acids other than DNA. In certain aspects, the nucleic acid sample comprises mitochondrial DNA, chloroplastic DNA and/or DNA from other cellular organelles.

In certain aspects, the above-described method further comprises: b) circularizing the amplification products; and c) amplifying the circular amplification products using primers which hybridize to the constant 5' priming portion. In certain aspects, the amplifying in step c) comprises performing multiple displacement amplification.

Also presented herein is a kit for amplifying a nucleic acid sample wherein, the kit comprises random amplification primers, the random amplification primers comprising a random 3' portion and a constant 5' priming portion, wherein the random 3' portion comprises at least one non-natural base selected from the group consisting of: 2-thio-dT and 2-amino-dA. In certain aspects, the kit further comprises a set of instructions for combining the set of amplification primers with a nucleic acid library and amplifying the nucleic acid library. In certain other aspects, the kit further comprises a DNA polymerase. In still other aspects, the set of random amplification primers is a mixture of primers.

Also presented herein is a method of creating a nucleic acid library from a genomic nucleic acid sample comprising: a) providing a set of amplification primers to a genomic nucleic acid sample wherein the set of amplification primers comprises a first plurality of random sequence primers, and providing a second plurality of species specific sequence primers configured to amplify defined genomic regions in the nucleic acid sample, wherein the species specific sequence primers are in equal or greater abundance compared to the random primers, and b) amplifying the genomic nucleic acid sample using the set of amplification primers, thereby creating a nucleic acid library.

In some aspects, of the above-described method the genomic nucleic acid sample comprises a genomic DNA. In certain other aspects, the genomic nucleic acid sample comprises a plurality of genomic DNAs. In still other aspects, the genomic nucleic acid sample comprises DNA from one or more economically important species. In some aspects, the genomic nucleic acid sample comprises DNA from one or more plants, fungi, protists bacteria and/or archaebacteria. In some aspects, the genomic nucleic acid sample comprises nucleic acids other than DNA. In certain aspects, the genomic nucleic acid sample comprises mitochondrial DNA, chloroplastic DNA and/or DNA from other cellular organelles.

In some embodiments of the above-described method, the genomic nucleic acid sample is from a mammal, such as a human or other economically relevant animal. In certain embodiments, the genomic nucleic acid sample is from an economically relevant plant.

In certain embodiments, the second plurality of species specific sequence primers comprise humanized sequences. In certain embodiments, the defined regions in a genomic nucleic acid sample comprise one or more of non-repetitive regions and/or highly represented regions of a genomic nucleic acid sample. In certain embodiments, the sequences of the plurality of species specific primers are distributed essentially evenly across the genomic nucleic acid such that hybridization of the species specific primers to the defined genomic nucleic acid regions is unbiased or, at least, less biased than previously known amplification methods.

In some embodiments of the above-described method, the plurality of species specific sequence primers are approximately 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides or 20 nucleotides in length. In certain embodiments, the species specific sequence primers are approximately 6 nucleotides, 7 nucleotides, 8 nucleotides or 9 nucleotides in length.

In some embodiments of the above-described method, the second plurality of primers is present at equal abundance with the first plurality of primers. In other embodiments, the second plurality of primers is present at greater abundance than the first plurality of primers. In some embodiments, the species specific sequence primers comprise species specific priming sequences for at least 100, at least 200, at least 300, at least 400, at least 500, at least 600, at least 700, at least 800, at least 900, at least 1000, at least 1200, at least 1400, at least 1600, at least 1800, at least 2000, at least 2200, at least 2400, at least 2600, at least 2800, at least 3000, at least 3500, at least 4000, at least 4500, at least 5000, at least 5500, at least 6000, at least 6500, at least 7000, at least 7500, at least 8000, at least 8500, at least 9000, at least 9500 or at least 10000 defined genomic regions.

DETAILED DESCRIPTION

Figure 1:
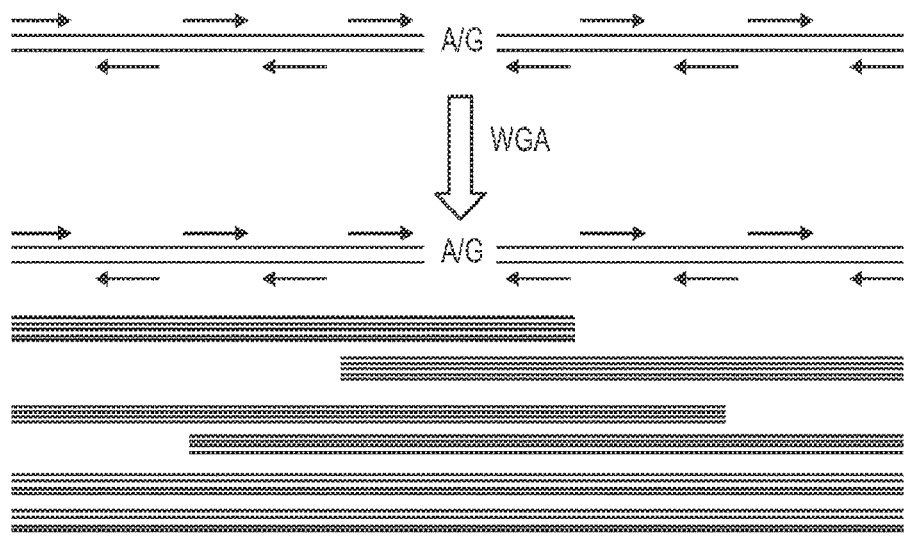
FIG. 1 is a schematic diagram that shows amplification of a region of genomic DNA containing a SNP using whole genome amplification (WGA) initiated by locus specific primers.

High throughput genotyping applications rely on efficient and relatively unbiased whole genome amplification (WGA) of analyzed genomic DNA. Random primer amplification and multiple displacement amplification (MDA) can be used in a large number of different applications from amplifying DNA, such as in WGA, to creating genomic sequencing libraries. The ability to amplify target DNA in a relatively unbiased manner is important in many applications, particularly in sequencing.

Random Primer Amplification (RPA) and MDA typically employ random n-mers (n=about 5 to about 18). The random n-mers can exhibit fourfold degeneracy at each position. The general methodology comprises random n-mer primers used in the presence of a strand-displacing polymerase, nucleotides, buffer and target to generate amplification of the original nucleic acid target sequence.

In reality, there is a significant difference in amplification efficiency of different regions of the genome due to, for example, local compositional and structural properties of genomic DNA. Therefore, regions of the genome can amplify at insufficient rates which would result in for example failure of genotyping or confusing genotyping data along such as, for example copy number variation discrepancies.

In addition, RPA and MDA of DNA and RNA often results in the introduction of one or more artifacts. For example, sequence bias can be introduced due to differential priming efficiency between AT-rich nucleotide sequences (AT-rich n-mers) compared to GC-rich nucleotide sequences (GC-rich n-mers). Further, formation of chimeras can occur due to mispriming of product strands on other product strands, or mispriming on the original target sequence for example. Additionally, primer-primer extension artifacts can arise.

Presented herein are novel approaches to reduce or eliminate these artifacts during random primer amplification of nucleic acids. As described in greater detail below, these approaches surprisingly lead to enhanced amplification and reduced bias across nucleic acid libraries.

Locus Specific Primers

Presented herein is an approach to amplify and/or improve the amplification efficiency of selected loci by supplementing a WGA reaction with locus specific oligonucleotides. Multiple oligonucleotides designed on one or two sides (e.g., upstream and downstream, 5' and 3', etc.) of a single site or multiple loci are used as primers in strand displacing DNA amplification reactions. A sufficient number of primers surrounding the regions of interest can be determined empirically and the length of locus specific primers can be optimized to ensure effective primer annealing during WGA. Locus specific primers can be either of equal length, shorter than, or longer than the random primers. Primers can be engineered by varying length to provide optimal annealing specificity. A skilled artisan will appreciate the methods of the art with regards to primer design. Standard genomic amplification protocols utilize random primers such as random 6-mers or 9-mers. However, for each specific genome of interest, the 6-mer or 9-mer sequences are NOT equally distributed across the genome; some of the sequences may occur in the genome more frequently than the others. As such, certain primer sequences may be under- or over-represented in the random primer pool. Thus, in certain embodiments, additional locus specific sequences, such as, for example, a set of 9-mers that are highly represented in the human genome can be added to a random primer pool to constitute an Enhanced Amplification Primer Pool (EAPP) in order to minimize the stochastic nature of priming and to amplify the whole genome in an unbiased way. As a result, this approach can lead to increases of genotyping call-rate and genome representation of sequencing.

One surprising discovery presented herein is that locus specific primers can be functional in a large background and excess of random primers. These specific primers can enhance the amplification of specific regions by either amplifying the region directly from genomic DNA, from random primer copied genomic DNA, or a combination thereof.

Accordingly, presented herein are methods of amplifying a nucleic acid sample that make use of locus specific primers in a mixture of random primers. In some embodiments, the methods can comprise providing a mixture of amplification primers to a nucleic acid library, the mixture comprising a plurality of random primers and a plurality of locus specific primers configured to amplify a plurality of predetermined regions of the nucleic acid library, and amplifying the nucleic acid library using the mixture of amplification primers.

Also presented herein is a method of creating a nucleic acid library from a genomic nucleic acid sample comprising:

a) providing a set of amplification primers to a genomic nucleic acid sample wherein the set of amplification primers comprises a first plurality of random sequence primers, and a second plurality of species specific sequence primers configured to amplify defined genomic regions in the nucleic acid sample, wherein the species specific sequence primers are in equal, lower, or greater abundance compared to the random primers, and b) amplifying the genomic nucleic acid sample using the set of amplification primers, thereby creating a nucleic acid library. In some embodiments, the species specific sequence primers are designed to hybridize to non-repetitive sequences of a targeted genome in order to minimize over-amplification of repetitive sequences. In some embodiments, the species specific sequence primers are designed so as to minimize cross-hybridization among the primers themselves. For example, species specific sequence primers can be designed to minimize the complementarities of the primers, especially in their 3'-ends. In some embodiments, the species specific sequence primers are designed to avoid or minimize hybridization with polymorphic sites in a genome. In some embodiments, the species specific sequence primers are designed to be evenly distributed across an entire genome. In some embodiments, the species specific sequence primers are designed to be evenly distributed across an entire chromosome. In some embodiments, the species specific sequence primers are designed to be evenly distributed across a targeted genomic region, such as a portion of a genome. In some embodiments, each particular species specific primer sequence is present at the same concentration as other species specific primer sequences in the second population. In other embodiments, each particular species specific primer sequence may be present at a different concentration as other species specific primer sequences in the second population.

In certain embodiments, as discussed in greater detail below, the genomic nucleic acid sample can be from a mammal, such as a human or other economically relevant animal. In certain embodiments, the genomic nucleic acid sample can be from an economically relevant plant. As used herein, the term economically relevant relates to animal or plant species used in agriculture, medicine, laboratory research, or any other endeavor that creates an economic relevance for the animal or plant species. Economically relevant plants are known in the art, and include, but are not limited to thale cress (*Arabidopsis thaliana*), corn (*Zea mays*), sorghum (*Sorghum bicolor*), oat (*Avena sativa*), wheat (*Triticum aestivum*), rice (*Oryza sativa*), canola (*Brassica campestris*), soybean (*Glycine max*) and cultivars, variants and hybrids thereof. Economically relevant animals are known in the art, and include, but are not limited to a mammal such as a rodent, mouse, rat, rabbit, guinea pig, ungulate, horse, sheep, pig, goat, cow, cat, dog, primate, human or non-human primate; a nematode such as *Caenorhabditis elegans*; an insect such as *Drosophila melanogaster*, mosquito, fruit fly, honey bee or spider; a fish such as zebrafish (*Danio rerio*); a reptile; or an amphibian such as a frog or *Xenopus laevis* as well as all of the other organisms disclosed herein.

In certain embodiments, the second plurality of species specific sequence primers comprise humanized sequences. In certain embodiments, the defined regions in a genomic nucleic acid sample comprise one or more of non-repetitive regions and highly represented repetitive regions of a genomic nucleic acid sample. In certain embodiments, the sequences of the plurality of species specific primers is distributed essentially evenly across the genomic nucleic acid such that hybridization of the species specific primers to the defined genomic nucleic acid regions is substantially unbiased. In some embodiments, the plurality of species specific primers is distributed in a relatively unbiased manner. In other embodiments, the plurality of species specific primers is distributed in a significantly unbiased manner. In still other embodiments, the plurality of species specific primers is distributed in an essentially unbiased manner. In yet other embodiments, the plurality of species specific primers is distributed in an unbiased manner.

In certain embodiments, the plurality of locus specific or species specific sequence primers comprises sequences of at least 100, at least 200, at least 300, at least 400, at least 500, at least 600, at least 700, at least 800, at least 900, at least 1000, at least 1200, at least 1400, at least 1600, at least 1800, at least 2000, at least 2200, at least 2400, at least 2600, at least 2800, at least 3000, at least 3500, at least 4000, at least 4500, at least 5000, at least 5500, at least 6000, at least 6500, at least 7000, at least 7500, at least 8000, at least 8500, at least 9000, at least 9500 or at least 10000 defined genomic regions. In specific embodiments, the random primers are in equal, lower, or greater abundance compared to the locus specific primers. As used herein, the term "abundance" refers to an amount of an entity. The amount may be described in terms of concentration, a term of art well known to those with ordinary skill. The relative abundance of primers in a reaction can be described, for example, using the concentration of primers. Concentration may be relative to a known standard or may be absolute. Thus, in some embodiments, the concentration of random primers is higher than the concentration of locus specific primers. In some embodiments, the concentration of random primers is about 1.1 times, 1.2 times, 1.3 times, 1.4 times, 1.5 times, 1.6 times, 1.7 times, 1.8 times, 1.9 times, 2.0 times, 2.5 times, 3.0 times, 3.5 times, 4.0 times, 4.5 times, 5.0 times, 5.5 times, 6.0 times, 6.5 times, 7.0 times, 7.5 times, 8.0 times, 8.5 times, 9.0 times, 9.5 times, 10.0 times, 11 times, 12 times, 13 times, 14 times, 15 times, 16 times, 17 times, 18 times, 19 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1000 times, 2000 times, 3000 times, 4000 times or about 5000 times or greater than the concentration of locus specific primers. In typical embodiments, the concentration of random primers is about 50 times to about 5000 times greater than the concentration of locus specific primers. Thus, in an embodiment where the concentration of random hexamers in an amplification reaction is 50 micromolar, the final concentration of locus specific primers in the reaction could be, for example, about 0.01 micromolar, about 0.02 micromolar, about 0.03 micromolar, about 0.04 micromolar, about 0.05 micromolar, about 0.06 micromolar, about 0.07 micromolar, about 0.08 micromolar, about 0.09 micromolar, about 0.1 micromolar, about 0.2 micromolar, about 0.3 micromolar, about 0.4 micromolar, or about 0.5 micromolar, per oligonucleotide.

In some embodiments, the plurality of random primers comprises nucleic acid primers that are any of a variety of random sequence lengths, as known in the art. For example, the plurality of random primers can comprise a random sequence that is 3, 4, 5, 6, 7, 8, 10, 11, 12, 13, 14, 15, 16, 17, 18, 19, 20 or more nucleotides long. In certain embodiments, the plurality of random primers can comprise random primers of various lengths. In certain embodiments, the plurality of random primers can comprise random primers that are of equal length. In certain embodiments, the plurality of random primers can comprise a random sequence that is about 5 to about 18 nucleotides long. In some embodiments, the plurality of random primers comprises random hexamers. Random primers, and particularly random hexamers, are commercially available and widely used in amplification reactions such as Multiple Displacement Amplification (MDA), as exemplified by REPLI-g whole genome amplification kits (QIAGEN, Valencia, Calif.). It will be appreciated that any suitable length of random primers may be used in the methods and compositions presented herein.

In some embodiments, the locus specific primers comprise nucleic acid primers that are any of a variety of sequence lengths, as known in the art. For example, the locus specific primers can comprise a locus specific sequence that is 3, 4, 5, 6, 7, 8, 10, 11, 12, 13, 14, 15, 16, 17, 18, 19, 20 or more nucleotides long. In certain embodiments, the locus specific primers can comprise locus specific primers of various lengths. In certain embodiments, the locus specific primers can comprise locus specific primers that are of equal length. In certain embodiments, the locus specific primers can comprise a locus specific sequence that is about 5 to about 18 nucleotides long. It will be appreciated that any suitable length of locus specific primers may be used in the methods and compositions presented herein. In certain preferred embodiments, the locus specific primers are 9 nucleotides in length. In some embodiments, locus specific primers are of equal length to the random primers. In some embodiments, the locus specific primers are shorter than the random primers. In still other embodiments, the locus specific primers are longer than the random primers. In some embodiments, the locus specific primers can be a combination of primer lengths, such as a mixture of locus specific primers comprising shorter, equal and longer primers as compared to the random primers.

In some embodiments, the random primers comprise exonuclease-resistant primers. In some embodiments, the locus specific primers comprise exonuclease-resistant primers. Exonuclease-resistant primers are especially useful when amplification reactions comprise a polymerase with exonuclease activity, such as phi29 DNA polymerase, which has inherent 3'→5' proofreading exonuclease activity. Exonuclease-resistant primers are known in the art, and can include, for example, phosphorothioate linkages and the like. In some embodiments, for example, a primer may possess one, two, three or more phosphorothioate linkages between nucleotides at the 3' end of the primer sequence. In some embodiments, the primer may comprise one or more modified nucleotides. The modified nucleotide may be a phosphorothioate nucleotide. In some embodiments, the modified nucleotide is a 3'-terminal nucleotide. In some embodiments, the modified nucleotide is located at a position other than the 3'-terminal position. When the modified nucleotide is located at positions other than the 3'-terminal end of a primer sequence, the 3'-terminal nucleotide of the primer may be removed by the 3'→5' exonuclease activity. For example, random primers comprising the sequences such as NNNN*N*N can be used in the methods and compositions provided herein (* represents a phosphorothioate bond between the nucleotides N). In some embodiments, at least a subset of the random primers comprise a 3' blocking group or otherwise lack a 3' OH group and cannot prime extension by a polymerase. For example, in certain situations, particular regions of a genome are over-amplified during whole genome amplification, while other regions are underrepresented. Thus, in one embodiment, a limited diversity of high excess exonuclease-resistant, 3' blocked primers are added to a random primer mix. The 3' blocked primers can be designed to hybridize to any region or regions where a reduction of overamplification is desired. The 3' blocked primers can be designed to hybridize to regions that are frequently found to be overrepresented in whole genome amplification. The 3' blocked primers can be designed to hybridize to highly repetitive regions in the genome which otherwise lead to unmappable reads. For example, 3' blocked hexamers can outcompete their unblocked counterparts that are present in a random hexamer pool and therefore block annealing and extension from these hexamers. The result is a reduction in regions of overamplification and a reduction in the representation of highly repetitive regions that lead to unmappable sequencing reads.

The term "random" as used throughout the present disclosure with respect to primers, oligonucleotides, polynucleotides and the like should be understood to refer to degeneracy at one or more positions of a nucleotide. Thus, in certain embodiments, the term random can refer to purely random distribution at all positions, where each position can be equally likely to be any one of the four standard nucleotides. In certain embodiments, the term random can refer to a random distribution at less than all of the nucleotide positions in the polynucleotide. In some embodiments, the term random can refer to a weighted random distribution at one or more positions, or all positions of a polynucleotide, where degeneracy is not equally distributed among the four standard nucleotides at each position defined as random. In some embodiments, the term random can refer to a biased distribution of the four standard nucleotides at one or more positions. Random polynucleotides can also be understood to include one or more base analogues as part of the nucleotides available for distribution at the one or more positions. Thus, in some embodiments, the plurality of random primers can be entirely random at each position of the primer. In some embodiments, the random sequence of a random primer can include interspersed positions having a fixed nucleotide or regions having a fixed sequence of two or more nucleotides, if desired.

Amplification Methods and Reagents

The methods provided herein comprise amplifying a nucleic acid sample using the mixture of amplification primers. As used herein, the terms "amplifying," "amplify," "amplification" and like terms refer to producing one or more copies of a single stranded or double stranded nucleic acid, or a portion thereof. In some embodiments, the methods provided herein can include a step of producing an amplified nucleic acid library under isothermal or thermal variable conditions. Exemplary isothermal amplification methods that can be used in a method of the present disclosure include, but are not limited to, Multiple Displacement Amplification (MDA) as exemplified by, for example Dean et al., Proc Natl. Acad. Sci USA 99:5261-66 (2002) or isothermal strand displacement nucleic acid amplification exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'->3' exo⁻ for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety.

Another nucleic acid amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993), incorporated herein by reference in its entirety. The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

A further approach that can be used to amplify gDNA in connection with the methods of the present disclosure is degenerate oligonucleotide primed polymerase chain reaction (DOP-PCR) under conditions such as, but not limited to, those described by Cheung et al., Proc. Natl. Acad. Sci. USA, 93:14676-79 (1996) or U.S. Pat. No. 5,043,272, the disclosures of which are incorporated herein by reference in their entireties. Low amounts of gDNA, for example, 15 pg of human gDNA, can be amplified to levels that are conveniently detected in the methods of the present disclosure. Reaction conditions used in the methods of Cheung et al. can be selected for production of an amplified representative population of genome fragments having near complete coverage of the human genome. Furthermore modified versions of DOP-PCR, such as those described by Kittler et al. in a protocol known as LL-DOP-PCR (Long products from Low DNA quantities-DOP-PCR) can be used to amplify gDNA in accordance with the present disclosure (Kittler et al., Anal. Biochem. 300:237-44 (2002), the disclosure of which is incorporated herein by reference in its entirety).

Primer-extension preamplification polymerase chain reaction (PEP-PCR) can also be used in a method of the present disclosure in order to amplify gDNA. Useful conditions for amplification of gDNA using PEP-PCR include, for example, those described in Casas et al., Biotechniques 20:219-25 (1996), incorporated herein by reference in its entirety.

The present methods are not limited to any particular amplification technique and amplification techniques described herein are exemplary only with regards to methods and embodiments of the present disclosure.

Generally, polymerase activity, including, for example, processivity and strand displacement activity, can be influenced by factors such as pH, temperature, ionic strength, and buffer composition. Those skilled in the art will know which types of polymerases and conditions can be used to obtain fragments having a desired length in view of that which is known regarding the activity of the polymerases as described, for example, in Eun, H. M., Enzymology Primer for Recombinant DNA Technology, Academic Press, San Diego (1996). Moreover, a skilled artisan will be able to determine appropriate polymerases and conditions by systematic testing using known assays, such as gel electrophoresis or mass spectrometry, to measure the length of amplified fragments.

E. coli Pol I or its Klenow fragment can be used for isothermal amplification of a genome to produce small genomic DNA fragments, for example, in a low salt (1=0.085) reaction incubated at a temperature between about 5° C. and 37° C. Exemplary buffers and pH conditions that can be used to amplify gDNA with Klenow fragment include, for example, 50 mM Tris HCl (pH 7.5), 5 mM $MgCl_2$, 50 mM NaCl, 50 µg/ml bovine serum albumin (BSA), 0.2 mM of each dNTP, 2 µg random primer (n=6), 10 ng gDNA template and 5 units of Klenow exo-incubated at 37° C. for 16 hours. Similar reaction conditions can be run where one or more reaction component is omitted or substituted. For example, the buffer can be replaced with 50 mM phosphate (pH 7.4) or other pH values in the range of about 7.0 to 7.8 can be used. A gDNA template to be amplified can be provided in any of a variety of amounts including, without limitation, those set forth previously herein. In an alternative embodiment, conditions for amplification can include, for example, 10 ng genomic DNA template, 2 mM dNTPs, 10 mM $MgCl_2$, 0.5 U/µl polymerase, 50 µM random primer (n=6) and isothermal incubation at 37° C. for 16 hours.

In particular embodiments, an amplification reaction can be carried out in two steps including, for example, an initial annealing step followed by an extension step. For example, 10 ng gDNA can be annealed with 100 µM random primer (n=6) in 30 µl of 10 mM Tris-Cl (pH 7.5) by brief incubation at 95° C. The reaction can be cooled to room temperature and an annealing step carried out by adding an equal volume of 20 mM Tris-Cl (pH 7.5), 20 mM $MgCl_2$, 15 mM dithiothreitol, 4 mM dNTPs and 1 U/µl Klenow exo- and incubating at 37° C. for 16 hrs. Although exemplified for Klenow-based amplification, those skilled in the art will recognize that separate annealing and extension steps can be used for amplification reactions carried out with other polymerases such as those set forth below.

In particular embodiments, primers having random annealing regions of different lengths (n) can be substituted in the Klenow-based amplification methods. For example, the n=6 random primers in the above exemplary conditions can be replaced with primers having other random sequence lengths including, without limitation, n=7, 8, 9, 10, 11 or 12 nucleotides. Again, although exemplified for Klenow-based amplification, those skilled in the art will recognize that random primers having different random sequence lengths (n) can be used for amplification reactions carried out with other polymerases such as those set forth below.

T4 DNA polymerase can be used for amplification of single stranded or denatured gDNA, for example, in 50 mM HEPES pH 7.5, 50 mM Tris-HCl pH 8.6, or 50 mM glycinate pH 9.7. A typical reaction mixture can also contain 50 mM KCl, 5 mM $MgCl_2$, 5 mM dithiothreitol (DTT), 40 µg/ml gDNA, 0.2 mM of each dNTP, 50 µg/ml BSA, 100 µM random primer (n=6) and 10 units of T4 polymerase incubated at 37° C. for at least one hour. Temperature cycling can be used to displace replicate strands for multiple rounds of amplification.

T7 polymerase is typically highly processive allowing polymerization of thousands of nucleotides before dissociating from a template DNA. Typical reaction conditions under which T7 polymerase is highly processive are 40 mM Tris-HCl pH 7.5, 15 mM $MgCl_2$, 25 mM NaCl, 5 mM DTT, 0.25 mM of each dNTP, 50 µg/ml single stranded gDNA, 100 µM random primer (n=6) and 0.5 to 1 unit of T7 polymerase. However, at temperatures below 37° C., processivity of T7 polymerase is greatly reduced. Processivity of T7 polymerase can also be reduced at high ionic strengths, for example, above 100 mM NaCl. Form II T7 polymerase is not typically capable of amplifying double stranded DNA. However, Form I T7 polymerase and modified T7 polymerase (SEQUENASE™ version 2.0 which lacks the 28 amino acid region Lys 118 to Arg 145) can catalyze strand displacement replication. Accordingly, small genome fragments can be amplified in a method of the present disclosure using a modified T7 polymerase or modified conditions such as those set forth above. In particular embodiments, SEQUENASE™ can be used in the presence of E. coli single stranded binding protein (SSB) for increased strand displacement. SSB can also be used to increase processivity of SEQUENASE™, if desired.

Taq polymerase is highly processive at temperatures around 70° C. when reacted with a 10 fold molar excess of template and random primer (n=6). An amplification reaction run under these conditions can further include a buffer such as Tris-HCl at about 20 mM, pH of about 7, about 1 to 2 mM $MgCl_2$, and 0.2 mM of each dNTP. Additionally a stabilizing agent can be added such as glycerol, gelatin, DMSO, betaine, BSA or a non-ionic detergent. Taq polymerase has low processivity at temperatures below 70° C. Accordingly, small fragments of gDNA can be obtained by using Taq polymerase at a low temperature in a method of the present disclosure, or in another condition in which Taq has low processivity. In another embodiment, the Stoffel Fragment, which lacks the N-terminal 289 amino acid residues of Taq polymerase and has low processivity at 70° C., can be used to generate relatively small gDNA fragments in a method of the present disclosure. Taq can be used to amplify single stranded or denatured DNA templates in a method of the present disclosure. Temperature cycling can be used to displace replicate strands for multiple rounds of amplification.

Those skilled in the art will recognize that the conditions for amplification with the various polymerases as set forth above are exemplary. Thus, minor changes that do not substantially alter activity can be made. Furthermore, the conditions can be substantively changed to achieve a desired amplification activity or to suit a particular application of the present disclosure.

The methods and compositions of the present disclosure can also be used with variants of the above-described polymerases, so long as they retain polymerase activity. Exemplary variants include, without limitation, those that have decreased exonuclease activity, increased fidelity, increased stability or increased affinity for nucleoside analogs. Exemplary variants as well as other polymerases that are useful in a method of the present disclosure include, without limitation, bacteriophage phi29 DNA polymerase (U.S. Pat. Nos. 5,198,543 and 5,001,050), exo(–)Bca DNA polymerase (Walker and Linn, Clinical Chemistry 42:1604-1608 (1996)), phage M2 DNA polymerase (Matsumoto et al., Gene 84:247 (1989)), phage phiPRD1 DNA polymerase (Jung et al., Proc. Natl. Acad. Sci. USA 84:8287 (1987)), exo(–)VENT™ DNA polymerase (Kong et al., J. Biol. Chem. 268.1965-1975 (1993)), T5 DNA polymerase (Chatterjee et al., Gene 97:13-19 (1991)), and PRD1 DNA polymerase (Zhu et al., Biochim. Biophys. Acta. 1219:267-276 (1994), the disclosures of which are incorporated herein by reference in their entireties).

A further polymerase variant that is useful with the methods and compositions of the present disclosure is a modified polymerase that, when compared to its wild type unmodified version, has a reduced or eliminated ability to add non-template directed nucleotides to the 3' end of a nucleic acid. Exemplary variants include those that may affect activity of the polymerase toward adding all types of nucleotides or one or more types of nucleotides such as pyrimidine nucleotides, purine nucleotides, A, C, T, U or G. Modifications can include chemical modification of amino acid groups in the polymerase or sequence mutations such as deletions, additions or replacements of amino acids. Examples of modified polymerases having reduced or eliminated ability to add non-template directed nucleotides to the 3' end of a nucleic acid are described, for example, in U.S. Pat. No. 6,306,588 or Yang et al., Nucl. Acids Res. 30:4314-4320 (2002), the disclosures of which are incorporated herein by reference in their entireties. In a particular embodiment, such a polymerase variant can be used in an SBE or ASPE detection method described herein.

The nucleic acid library amplified by the methods and compositions described herein can comprise essentially any type of nucleic acid. In some embodiments of the present methods and compositions described herein, the nucleic acid sample comprises a genome, genome fragment, a mixture of genomes or a mixture of genome fragments. The term genome fragment is intended to mean an isolated nucleic acid molecule having a sequence that is substantially identical to a portion of a chromosome. A chromosome is understood to be a linear or sometimes circular nucleic acid-containing body of a virus, prokaryotic organism, or eukaryotic nucleus that contains most or all of the replicated genes. A population of genome fragments can include sequences identical to substantially an entire genome or a portion thereof. A genomic fragment can have, for example, a sequence that is substantially identical to at least about 25, 50, 70, 100, 200, 300, 400, 500, 600, 700, 800, 900 or 1000 or more nucleotides of a chromosome. A genome fragment can be DNA, RNA, or an analog thereof. It will be understood by those skilled in the art that an RNA sequence and DNA chromosome sequence that differ by the presence of uracils in place of thymines are substantially identical in sequence.

In some embodiments, the nucleic acid sample comprises RNA. In some embodiments of the present systems and methods described herein, the nucleic acid sample comprises DNA. The DNA utilized herein is not limited by type but typically comprises genomic DNA (gDNA) or cDNA. Genomic DNA can refer to actual nucleic acid material isolated from an organism, or alternatively, one or more copies of portions of the genome of an organism or one or more copies of the entire genome of an organism. For example, genomic DNA can refer to a copy of a fragment of genomic DNA that has been isolated from an organism. In some embodiments, genomic DNA is isolated from a cell or other material and fragmented. The fragments are then copied or otherwise amplified. Although this amplified material may contain replica sequences rather than nucleic acid molecules isolated directly from the organism, this material is still referred to herein as genomic DNA or DNA obtained or derived from the genome of an organism. As such, the genomic DNA described herein can include fragments or copies of fragments of genomic DNA sequences. In some embodiments, the sample is a forensic sample containing only trace amounts of nucleic acid material. In some embodiments, the sample bisulfite converted genomic DNA and sequence-specific primers are designed so specifically amplify the bisulfite converted sequences.

For example, a DNA sample that is amplified according to the methods provided herein can be a genome such as those set forth above or other DNA templates such as mitochondrial DNA or some subset of genomic DNA. One non-limiting example of a subset of genomic DNA is one particular chromosome or one region of a particular chromosome.

The methods and compositions of the present disclosure are useful in a number of applications including, for example, single cell sperm haplotype analysis, genotyping of large numbers of individuals in a high-throughput format, identification of new haplotypes, phasing of haplotypes, de novo sequencing, forensic, disease determination, health care, therapeutic efficacy determinations, disease diagnosis and prognosis to name but a few. Furthermore, the present disclosure reduces the amount of DNA or RNA sample required in many current array assays. Further still, improved array sensitivity available with the present disclosure can lead to, for example reduced sample requirements, improved LOD scoring ability, and greater dynamic range.

The methods and compositions of the present disclosure can be used to amplify genomic DNA (gDNA) from any organism. The methods are ideally suited to the amplification and analysis of large genomes such as those typically found in eukaryotic unicellular and multicellular organisms. Exemplary eukaryotic gDNA that can be used in a method of the present disclosure includes, without limitation, that from a mammal such as a rodent, mouse, rat, rabbit, guinea pig, ungulate, horse, sheep, pig, goat, cow, cat, dog, primate, human or non-human primate; a plant such as *Arabidopsis thaliana*, corn (*Zea mays*), sorghum, oat, wheat, rice (*Oryza sativa*), canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish (*Danio rerio*); a reptile; an amphibian such as a frog or *Xenopus laevis*; a fungus such as *Dictyostelium discoideum, Pneumocystis carinii, Takifugu rubripes, Saccharamoyces cerevisiae* or *Schizosaccharomyces pombe*; or a parasitic, disease causing organism such as *Plasmodium falciparum*. A method of the present disclosure can also be used to detect typable loci of smaller genomes such as those from a prokaryote such as a bacterium, *Escherichia coli*, staphylococci or *Mycoplasma pneumoniae*; an Archae; a virus such as Hepatitis C virus or human immunodeficiency virus (HIV); or a viroid.

A genomic DNA used in connection with the methods and compositions of the present disclosure can have one or more chromosomes. For example, a prokaryotic genomic DNA including one chromosome can be used. Alternatively, a eukaryotic genomic DNA including a plurality of chromosomes can be used in a method of the present disclosure. Thus, the methods can be used, for example, to amplify or detect typable loci of a genomic DNA having n equal to 2 or more, 4 or more, 6 or more, 8 or more, 10 or more, 15 or more, 20 or more, 23 or more, 25 or more, 30 or more, or 35 or more chromosomes, where n is the haploid chromosome number and the diploid chromosome count is 2n. The size of a genomic DNA used in a method of the present disclosure can also be measured according to the number of base pairs or nucleotide length of the chromosome complement. Exemplary size estimates for some of the genomes that are useful in the present disclosure are about 3.1 Gbp (human), 2.7 Gbp (mouse), 2.8 Gbp (rat), 1.7 Gbp (zebrafish), 165 Mbp (fruitfly), 13.5 Mbp (*S. cerevisiae*), 390 Mbp (fugu), 278 Mbp (mosquito) or 103 Mbp (*C. elegans*). Those skilled in the art will recognize that genomes having sizes other than those exemplified above including, for example, smaller or larger genomes can be used in a method of the present disclosure.

Genomic DNA can be isolated from one or more cells, bodily fluids or tissues. Known methods can be used to obtain a bodily fluid such as blood, sweat, tears, lymph, urine, saliva, semen, cerebrospinal fluid, feces or amniotic fluid. Similarly known biopsy methods can be used to obtain cells or tissues such as buccal swab, mouthwash, surgical removal, biopsy aspiration or the like. Genomic DNA can also be obtained from one or more cell or tissue in primary culture, in a propagated cell line, a fixed archival sample, forensic sample or archeological sample.

Exemplary cell types from which gDNA can be obtained for use in connection with the methods and compositions of the present disclosure include, without limitation, a blood cell such as a B lymphocyte, T lymphocyte, leukocyte, erythrocyte, macrophage, or neutrophil; a muscle cell such as a skeletal cell, smooth muscle cell or cardiac muscle cell; germ cell such as a sperm or egg; epithelial cell; connective tissue cell such as an adipocyte, fibroblast or osteoblast; neuron; astrocyte; stromal cell; kidney cell; pancreatic cell; liver cell; or keratinocyte. A cell from which gDNA is obtained can be at a particular developmental level including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Other cells include a bone marrow stromal cell (mesenchymal stem cell) or a cell that develops therefrom such as a bone cell (osteocyte), cartilage cells (chondrocyte), fat cell (adipocyte), or other kinds of connective tissue cells such as one found in tendons; neural stem cell or a cell it gives rise to including, for example, a nerve cells (neuron), astrocyte or oligodendrocyte; epithelial stem cell or a cell that arises from an epithelial stem cell such as an absorptive cell, goblet cell, Paneth cell, or enteroendocrine cell; skin stem cell; epidermal stem cell; or follicular stem cell. Generally any type of stem cell can be used including, without limitation, an embryonic stem cell, adult stem cell, or pluripotent stem cell.

A cell from which a gDNA sample is obtained for use in connection with the methods and compositions of the present disclosure can be a normal cell or a cell displaying one or more symptom of a particular disease or condition. Thus, a gDNA used in a method of the present disclosure can be obtained from a cancer cell, neoplastic cell, necrotic cell or the like. Those skilled in the art will know or be able to readily determine methods for isolating gDNA from a cell, fluid or tissue using methods known in the art such as those described in Sambrook et al., Molecular Cloning: A Laboratory Manual, 3rd edition, Cold Spring Harbor Laboratory, New York (2001) or in Ausubel et al., Current Protocols in Molecular-Biology, John Wiley and Sons, Baltimore, Md. (1998).

A gDNA can be prepared for use in a method of the present disclosure by lysing a cell that contains the DNA. Typically, a cell is lysed under conditions that substantially preserve the integrity of the cell's gDNA. In particular, exposure of a cell to alkaline pH can be used to lyse a cell in a method of the present disclosure while causing relatively little damage to gDNA. Any of a variety of basic compounds can be used for lysis including, for example, potassium hydroxide, sodium hydroxide, and the like. Additionally, relatively undamaged gDNA can be obtained from a cell lysed by an enzyme that degrades the cell wall. Cells lacking a cell wall either naturally or due to enzymatic removal can also be lysed by exposure to osmotic stress. Other conditions that can be used to lyse a cell include exposure to detergents, mechanical disruption, sonication heat, pressure differential such as in a French press device, or Dounce homogenization. Agents that stabilize gDNA can be included in a cell lysate or isolated gDNA sample including, for example, nuclease inhibitors, chelating agents, reducing reagents, salts buffers and the like. Methods for lysing a cell to obtain gDNA can be carried out under conditions known in the art as described, for example, in Sambrook et al., supra (2001) or in Ausubel et al., supra, (1998).

In particular embodiments of the present disclosure, a crude cell lysate containing gDNA can be directly amplified or detected without further isolation of the gDNA. Alternatively, a gDNA can be further isolated from other cellular components prior to amplification or detection. Accordingly, a detection or amplification method of the present disclosure can be carried out on purified or partially purified gDNA. Genomic DNA can be isolated using known methods including, for example, liquid phase extraction, precipitation, solid phase extraction, chromatography and the like. Such methods are often referred to as minipreps and are described for example in Sambrook et al., supra, (2001) or in Ausubel et al., supra, (1998) or available from various commercial vendors including, for example, Qiagen (Valencia, Calif.) or Promega (Madison, Wis.).

A method or composition of the present disclosure can be used to produce an amplified genome from a small number of genome copies. Accordingly, small tissue samples or other samples having relatively few cells, for example, due to low abundance, biopsy constraints or high cost, can be sequenced, genotyped or evaluated on a genome-wide scale. Methods and compositions of the present disclosure can also be used to produce an amplified genome from a single native genome copy obtained, for example, from a single cell. In other exemplary embodiments of the present disclosure, an amplified genome can be produced from larger number of copies of a native genome including, but not limited to, about 1,000 copies (for a human genome, approximately 3 nanograms of DNA) or fewer, 10,000 copies or fewer, $1\times10^5$ copies (for a human genome, approximately 300 nanograms of DNA) or fewer, $5\times10^5$ copies or fewer, $1\times10^6$ copies or fewer, $1\times10^8$ copies or fewer, $1\times10^{10}$ copies or fewer, or $1\times10^{12}$ copies or fewer.

Primers

A primer used in connection with a method or composition of the present disclosure can have any of a variety of compositions or sizes, so long as it has the ability to hybridize to a template nucleic acid with sequence specificity and can participate in replication of the template. For example, a primer can be a nucleic acid having a native structure or an analog thereof. A nucleic acid with a native structure generally has a backbone containing phosphodiester bonds and can be, for example, deoxyribonucleic acid or ribonucleic acid. An analog structure can have an alternate backbone including, without limitation, phosphoramide (see, for example, Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (see, for example, Mag et al., Nucleic Acids Res. 19:1437 (1991); and U.S. Pat. No. 5,644,048), phosphorodithioate (see, for example, Briu et al., J. Am. Chem. Soc. 11 1:2321 (1989), O-methylphophoroamidite linkages (see, for example, Eckstein, Oligonucleotides and Analogues: A Practical Approach, Oxford University Press), and peptide nucleic acid backbones and linkages (see, for example, Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996)). Other analog structures include those with positive backbones (see, for example, Denpcy et al., Proc. Natl. Acad. Sci. USA 92:6097 (1995); non-ionic backbones (see, for example, U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Left. 4:395 (1994); Jeffs et al., J. Biomolecular NMR 34:17 (1994); Tetrahedron Lett. 37:743 (1996)) and non-ribose backbones, including, for example, those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Analog structures containing one or more carbocyclic sugars are also useful in the methods and are described, for example, in Jenkins et al., Chem. Soc. Rev. (1995) pp 169-176. Several other analog structures that are useful in the present disclosure are described in, for example Rawls, C & E News Jun. 2, 1997 page 35.

A nucleic acid useful in connection with the methods and/or compositions of the present disclosure can contain a non-natural sugar moiety in the backbone. Exemplary sugar modifications include but are not limited to 2' modifications such as addition of halogen, alkyl, substituted alkyl, allcaryl, arallcyl, O-allcaryl or O-aralkyl, SH, SCH3, OCN, Cl, Br, CN, CF3, OCF3, SOCH3, SO2 CH3, ONO2, NO$_2$, N3, NH2, heterocycloallcyl, heterocycloallcaryl, aminoallcylamino, polyallcylamino, substituted silyl, and the like. Similar modifications can also be made at other positions on the sugar, particularly the 3' position of the sugar on the 3' terminal nucleotide or in 2'-5' linked oligonucleotides and the 5' position of 5' terminal nucleotide.

A nucleic acid used in connection with the methods and/or compositions of the present disclosure can also include native or non-native bases. In this regard a native deoxyribonucleic acid can have one or more bases selected from the group consisting of adenine, thymine, cytosine or guanine and a ribonucleic acid can have one or more bases selected from the group consisting of uracil, adenine, cytosine or guanine. Exemplary non-native bases that can be included in a nucleic acid, whether having a native backbone or analog structure, include, without limitation, inosine, xathanine, hypoxathanine, isocytosine, isoguanine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine, 8-oxoguanine, or the like. A particular embodiment can utilize isocytosine and isoguanine in a nucleic acid in order to reduce non-specific hybridization, as generally described in U.S. Pat. No. 5,681, 702.

A non-native base used in a nucleic acid in connection with the methods and/or compositions of the present disclosure can have universal base pairing activity, wherein it is capable of base pairing with any other naturally occurring base. Exemplary bases having universal base pairing activity include, but are not limited to 3-nitropyrrole and 5-nitroindole. Other bases that can be used include those that have base pairing activity with a subset of the naturally occurring bases such as inosine which base pairs with cytosine, adenine or uracil.

A nucleic acid having a modified or analog structure can be used in connection with the methods and/or compositions of the present disclosure, for example, to facilitate the addition of labels, or to increase the stability or half-life of the molecule under amplification conditions or other conditions used in accordance with the present disclosure. As will be appreciated by those skilled in the art, one or more of the above-described nucleic acids can be used in connection with the methods and/or compositions of the present disclosure, including, for example, as a mixture including molecules with native or analog structures. In addition, a nucleic acid primer used in the present disclosure can have a structure desired for a particular amplification technique used in the present disclosure such as those set forth below.

Those skilled in the art will recognize that specificity of hybridization is generally increased as the length of the nucleic acid primer is increased. Thus, a longer nucleic acid primer can be used, for example, to increase specificity or reproducibility of replication, if desired. Accordingly, a nucleic acid used in a method of the present disclosure can be at least 5, 6, 7, 8, 9, 10, 11, 12, 13, 14, 15, 16, 17, 18, 19, 20, 25, 30, 35, 40, 50, 60, 70, 80, 90, 100, 200, 300, 400, 500 or more nucleotides long. Those skilled in the art will recognize that a nucleic acid probe used in the present disclosure can also have any of the exemplary lengths set forth above.

In particular embodiments, a population of nucleic acids used in connection with the methods and/or compositions of the present disclosure can include members with sequences that are designed based on rational algorithms or processes. Similarly, a population of nucleic acids can include members each having at least a portion of their sequence designed based on rational algorithms or processes. Rational design algorithms or processes can be used to direct synthesis of a nucleic acid product having a discrete sequence or to direct synthesis of a nucleic acid mixture that is biased to preferentially contain particular sequences.

Using rational design methods, sequences for nucleic acids in a population can be selected, for example, based on known sequences in the gDNA to be amplified or detected. The sequences can be selected such that the population preferentially includes sequences that hybridize to gDNA with a desired coverage. For example, a population of primers can be designed to preferentially include members that hybridize to a particular chromosome or portion of a gDNA such as coding regions or non coding regions. Other properties of a population of nucleic acids can also be selected to achieve preferential hybridization at positions along a gDNA sequence that are at a desired average, minimum or maximum length from each other. For example, primer length can be selected to hybridize and prime at least about every 64, 256, 1000, 4000, 16000 or more bases from each other along a gDNA sequence.

Nucleic acids useful in connection with the methods and/or compositions of the present disclosure can also be designed to preferentially omit or reduce sequences that hybridize to particular sequences in a gDNA to be amplified or detected such as known repeats or repetitive elements including, for example, Alu repeats. Accordingly, a single probe or primer such as one used in arbitrary-primer amplification can be designed to include or exclude a particular sequence. Similarly a population of probes or primers, such as a population of primers used for random primer amplification, can be synthesized to preferentially exclude or include particular sequences such as Alu repeats. A population of random primers can also be synthesized to preferentially include a higher content of G and/or C nucleotides compared to A and T nucleotides. The resulting random primer population will be GC rich and therefore have a higher probability of hybridizing to high GC regions of a genome such as gene coding regions of a human genome which typically have a higher GC content than non-coding gDNA regions. Conversely, AT-rich primers can be synthesized to preferentially amplify or anneal to AT-rich regions such as non-coding regions of a human genome. Other parameters that can be used to influence nucleic acid design include, for example, preferential removal of sequences that render primers self complementary, prone to formation of primer dimers or prone to hairpin formation or preferential selection of sequences that have a desired maximum, minimum or average T. Exemplary methods and algorithms that can be used in the present disclosure for designing probes include those described in US 2003/0096986A1, the disclosure of which is incorporated herein by reference in its entirety.

Primers in a population of random primers can have a region of identical sequence such as a universal tail. A universal tail can include a universal priming site for a subsequent amplification step or a site that anneals to a particular binding agent useful for isolating or detecting amplified sequences. Methods for making and using a population of random primers with universal tails are described, for example, in Singer et al., Nucl. Acid. Res. 25:781-786 (1997) or Grothues et al., Nucl. Acids Res. 21:1321-2 (1993).

Those skilled in the art will recognize that any of a variety of nucleic acids used in connection with the methods and/or compositions of the present disclosure such as probes can have one or more of the properties, or can be produced, as set forth above including in the examples provided with respect to primers.

AT-Rich Primers

Sequence bias due to differential priming efficiency between AT-rich vs. GC-rich random primers (n-mers) can be reduced or minimized according to any of a variety of novel approaches presented herein. One of these approaches is to bias the composition of a random n-mer mix such that AT-rich sequences are present at a higher concentration that would be found in a true random mix of n-mers. Accordingly, presented herein is a method of creating a nucleic acid library from a nucleic acid sample, the method comprising: amplifying a nucleic acid sample with an AT-rich set of random amplification primers. In certain aspects, the AT-rich set of random amplification primers is a mixture of primers. In certain aspects, the nucleic acid sample comprises a genomic DNA. In certain aspects, the genomic DNA comprises human DNA. In certain aspects, the nucleic acid sample comprises a plurality of genomic DNAs.

Typically during oligonucleotide synthesis of random n-mers, the final base degeneracy is roughly of equal proportions between the four bases: ~25% A, ~25% C, ~25% G, and ~25% T. However, according to the methods and/or compositions presented herein, any amount of degeneracy for a given base can be adjusted during randomized oligonucleotide synthesis. Methods of adjusting the amount of degeneracy of a given base during oligonucleotide synthesis are known in the art, and can be accomplished by, for example, adjusting the concentrations of one or more nucleoside phosphoramidite solutions higher or lower during batch oligonucleotide synthesis. Other approaches to modify the proportion of bases during random oligonucleotide synthesis or to obtain a mix of n-mers with a biased proportion of bases are known in the art.

Thus, in certain aspects, the overall composition of the AT-rich set of random amplification primers is greater than 25% A and 25% T. In certain embodiments, the AT-rich set of random amplification primers comprises the base 'A' in a proportion of about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or greater than about 50% of the total bases in the random mix of amplification primers. In certain embodiments, the AT-rich set of random amplification primers comprises the base 'T' in a proportion of about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or greater than about 50% of the total bases in the random mix of amplification primers. In certain typical embodiments, the AT-rich set of random amplification primers comprises about 30% A, about 20% C, about 20% G, and about 30% T. In certain typical embodiments, the AT-rich set of random amplification primers comprises about 35% A, about 15% C, about 15% G, and about 35% T. In certain other embodiments, the AT-rich set of random amplification primers are about 3, 4, 5, 6, 7, 8, 9, 10, 11, 12, 13, 14, 15, 16, 17, 18, 19, 20, 21, 22, 23, 24, 25, 26, 27, 28, 29 or greater than about 30 nucleotides in length. It will be appreciated that the exact composition of each base in a mixture of n-mers can be adjusted as needed to generate a desired level of amplification uniformity across a nucleic acid target such as genomic DNA. Further examples are presented in Example 6 below.

Also presented herein is a kit for amplifying a nucleic acid sample, the kit comprising an AT-rich set of random amplification primers. In certain aspects, the kit further comprises a set of instructions for combining the set of amplification primers with a nucleic acid library and amplifying the nucleic acid library. In certain aspects, the kit further comprises a DNA polymerase. In certain aspects, the AT-rich set of random amplification primers is a mixture of primers.

AT-Rich 5' Tails

Another novel approach to reduce or minimize sequence bias due to differential priming efficiency between AT-rich vs. GC-rich random primers (n-mers) is to add degenerate AT-rich 5' tails to a mix of random amplification primers. Thus, although the 5' tail is AT-rich, the remaining 3' portion of the amplification primers in the mixture are partially or totally degenerate and may or may not be AT-rich. Accordingly, presented herein is a method of creating a nucleic acid library from a nucleic acid sample, the method comprising: a) amplifying a nucleic acid sample with a set of random amplification primers, the random amplification primers comprising AT-rich 5' tails. In certain aspects, the set of random amplification primers is a mixture of primers.

The length of the AT-rich 5' tail can be any length appropriate to generate a desired level of amplification uniformity across a nucleic acid target such as genomic DNA. In certain aspects, the AT-rich 5' tail can be about 3, 4, 5, 6, 7, 8, 9, 10, 11, 12, 13, 14, 15, 16, 17, 18, 19, 20, 21, 22, 23, 24, 25, 26, 27, 28, 29 or greater than about 30 nucleotides in length. The 5' tail can be any 5' portion of an oligonucleotide. For example, the 5' tail can comprise the 5' portion that is about 2, 3, 4, 5, 6, 7, 8, 9, 10, 11, 12, 13, 14, 15, 16, 17, 18, 19, 20, 21, 22, 23, 24, 25, 26, 27, 28, 29 or greater than about 30 nucleotides of an oligonucleotide that is about 3, 4, 5, 6, 7, 8, 9, 10, 11, 12, 13, 14, 15, 16, 17, 18, 19, 20, 21, 22, 23, 24, 25, 26, 27, 28, 29 or greater than about 30 nucleotides in length. Thus, in certain aspects, the overall composition of the AT-rich set of random amplification primers is greater than 25% A and 25% T. In certain embodiments, the AT-rich 5' tail comprises the base 'A' in a proportion of about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or greater than about 50% of the total bases in the random mix of amplification primers. In certain embodiments, the AT-rich 5' tail comprises the base 'T' in a proportion of about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or greater than about 50% of the total bases in the random mix of amplification primers. In certain typical embodiments, the AT-rich 5'tail comprises 30% A, 20% C, 20% G, and 30% T. In certain typical embodiments, the AT-rich 5'tail comprises 35% A, 15% C, 15% G, and 35% T. In certain typical embodiments, the AT-rich 5'tail comprises 40% A, 10% C, 10% G, and 40% T. In certain typical embodiments, the AT-rich 5'tail comprises 50% A and 50% T.

As an example, a degenerate 9-mer sequence could be $[W]_m[N]_9$, where W=[A/T] degeneracy, m=an integer from 0 to 20, and N=any base. Thus, for example, one particular instance may be: 5'-WWWNNNNNNNNN-3'. This particular random n-mer has 9 totally degenerate positions at the 3' end of the primer, and 3 [A/T] wobble bases at the 5' end. Further examples are presented in Example 6 below.

In certain aspects, the nucleic acid sample comprises a genomic DNA. In certain aspects, the genomic DNA comprises human DNA. In certain aspects, the nucleic acid sample comprises a plurality of genomic DNAs.

Also presented herein is a kit for amplifying a nucleic acid sample, the kit comprising a set of random amplification primers, the random amplification primers comprising AT-rich 5' tails. In certain aspects, the kit further comprises a set of instructions for combining the set of amplification primers with a nucleic acid library and amplifying the nucleic acid library. In certain aspects, the kit further comprises a DNA polymerase. In certain aspects, the set of random amplification primers is a mixture of primers.

Degenerate 5' Tail

Another novel approach to reduce or minimize sequence bias due to differential priming efficiency between AT-rich vs. GC-rich random primers (n-mers) is to use variable length n-mers with degenerate 5' tails that are proportional in length to the A/T content. Accordingly, presented herein is a method of creating a nucleic acid library from a nucleic acid sample, the method comprising: amplifying a nucleic acid sample with a set of variable-length random amplification primers, wherein each primer comprises a random 3' portion and a degenerate 5' tail, the degenerate 5' tail proportional in length to the A/T content of the random 3' portion of the primer. In certain embodiments, this utilizes individual synthesis of all n-mer sequences, rather than randomized batch synthesis of a mixture of oligonucleotides. For example, in one embodiment, using W(A/T) and S(C/G) degenerate bases, a 6-mer variable length n-mer would require $2^6$ or 64 different syntheses. Likewise, a 7-mer would require 128 individual syntheses.

The approach described above enables normalization of $T_m$ of the individual oligonucleotides in a mixture of oligonucleotides. An exemplary approach for a mixture of n-mers is presented in the table below.

| 0 W | 1 W | 2 W | 3 W | 4 W | 5 W | 6 W |
|---|---|---|---|---|---|---|
| 0 | N | N | NN | NN | NNN | NNN |

As set forth in the above table, an n-mer having 0 W (A/T) content would require the addition of 0 degenerate bases on the 5' end of the n-mer. Likewise, an n-mer having 3 W (A/T) content would require the addition of 2 degenerate bases (NN) on the 5' end of the n-mer. Similarly, an n-mer having 6 W (A/T) content would require the addition of 3 degenerate bases (NNN) on the 5' end of the n-mer. Thus, for example, WWWWWW (6W) is assigned a 3 base n-mer tail: 5'-NNNWWWWWW, and WWSSSWW (4W) is assigned a 2 base n-mer tail: 5' NNWWSSWW, and similarly, SSSSWW (2W) is assigned a 1 base n-mer tail: 5'NSSSSWW. This concept is applied to a random 7-mer in Example 7 below.

Figure 5:
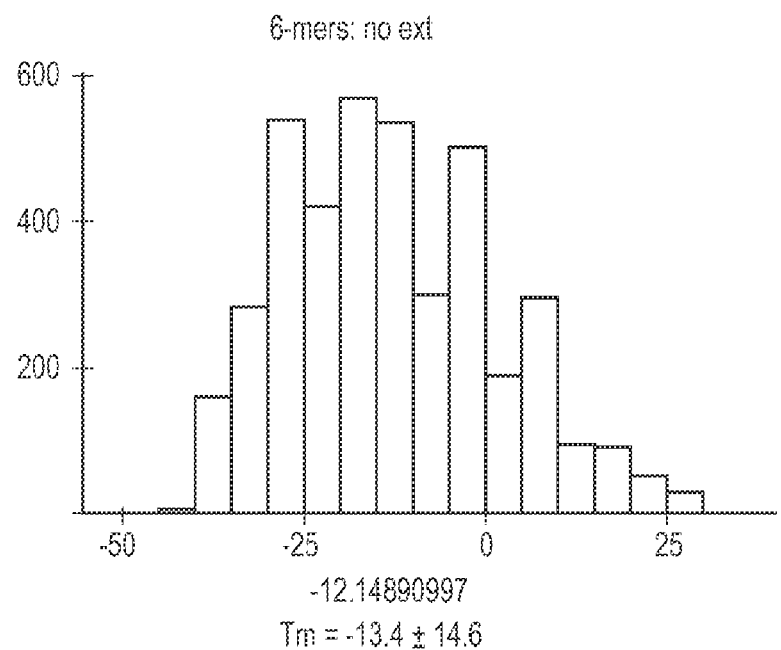
FIG. 5 shows a comparison of Tm of two primer mixes, demonstrating normalization of Tm by addition of a number of 5' terminal bases proportional to the AT content of a 6-mer.
Figure 5:
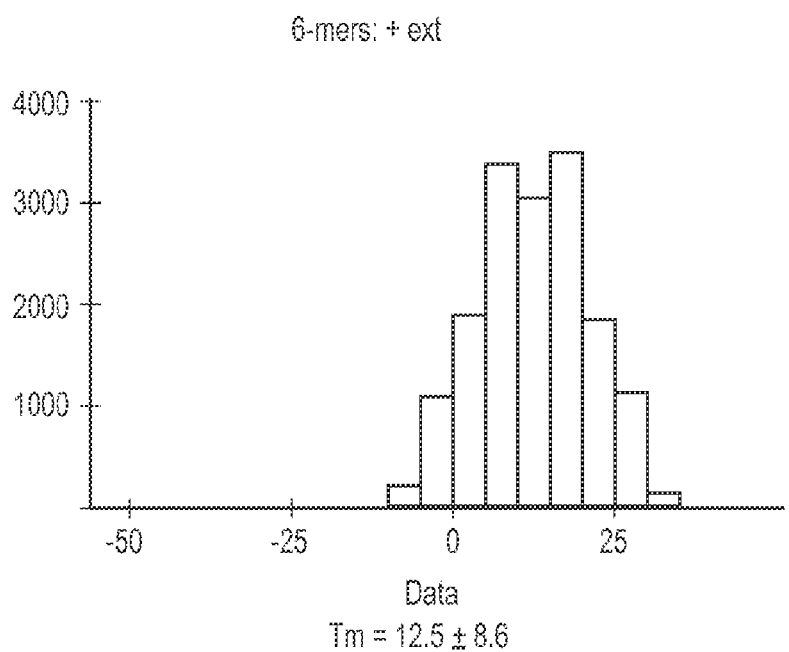

As a result of the addition of degenerate bases to the 5' end of an n-mer as set forth above, normalization of the Tms of a primer mixture can be achieved, as set forth, for example, in FIG. 5.

Also presented herein is a kit for amplifying a nucleic acid sample, the kit comprising a set of variable-length random amplification primers, wherein each primer comprises a random 3' portion and a degenerate 5' tail, the degenerate 5' tail proportional in length to the A/T content of the random 3' portion of the primer. In certain aspects, the kit further comprises a set of instructions for combining the set of amplification primers with a nucleic acid library and amplifying the nucleic acid library. In certain aspects, the kit further comprises a DNA polymerase. In certain aspects, the set of variable-length random amplification primers is a mixture of primers.

Primers with Base Analogues to Normalize Tm and Prevent Primer-Primer Interactions Another novel approach to reduce or minimize sequence bias due to differential priming efficiency between AT-rich vs. GC-rich random primers (n-mers) is to employ base analogues to normalize the Tm of n-mers differing in AT content. Accordingly, presented herein is a method of creating a nucleic acid library from a nucleic acid sample, the method comprising: amplifying a nucleic acid sample with a set of $T_m$-normalized amplification primers, wherein each primer of the set of $T_m$-normalized amplification primers comprises one or more base analogues that normalize the $T_m$ of each primer to the $T_m$ of other primers in the set of primers. In certain aspects, the set of $T_m$-normalized amplification primers is a mixture of primers.

The use of pseudo-complementary base pairs such as 2-thio-dT and 2-amino-dA that exhibit limited affinity for its complementary nucleotide in hybridization reactions are useful in methods disclosed herein. In RPA and MDA reactions, the use of random primer with pseudo-complementary bases helps prevent primer-primer amplification artifacts. Primer-primer amplification artifacts are one of the major obstacles to obtaining efficient WGA from low input amounts of nucleic acids since the primer-primer amplification can compete with amplification of the target DNA.

Thus, the incorporation of pseudo-complementary bases is particularly advantageous when amplification is performed using low amounts of input DNA, for example during single cell amplification. Additional advantages of incorporation of pseudo-complementary bases includes, for example normalizing $T_m$s as described above. It will be appreciated that base analogues that form additional or fewer hydrogen bonds during hybridization can be incorporated into a primer set to adjust the overall Tm of the primer set. In some embodiments, the base analogue is a non-natural base in the primer that may or may not form hydrogen bonds with its complement, but may prevent amplification across the non-natural base keeping the functionality of the primer intact. Additional non-natural bases that are suitable in the methods and compositions provided herein are known to those of skill in the art, as exemplified by Hoshika et al., Angew. Chem. Int. Ed. (2010) 49:5554, the content of which is incorporated by reference in its entirety. Other examples of nucleotide analogues or base analogues which can be used for these purposes include, for example, abasic nucleotides that create a gap, such that hydrogen bonding is reduced during hybridization.

For example, 2-amino-dA forms an additional hydrogen bond with thymidine, thereby leading to duplex stabilization with a melting temperature increase of 3° C. As another example, the N4-ethyl analogues of dC (N4-Et-dC) hybridizes specifically to natural guanine, but the stability of the base pair is reduced to about the level of an AT base pair. In this manner, a random n-mer using N4-Et-dC to replace G in one or more positions can decrease GC priming bias. Likewise, a random n-mer using 2-amino-dA to replace A in one or more positions may decrease GC priming bias. Similarly, both N4-Et-dC could be used together with 2-amino-dA to replace A and C in one or more positions to decrease GC priming bias. It will be appreciated that any base analogue that reduces or increases the stability of a base pair can be used to adjust the $T_m$ of a primer set. Thus, for example, base analogues including, but not limited to 2-thio-dT, 2-amino-dA, N4-Et-dC, and 7-deaza-G can be used in connection with the methods and/or compositions presented herein. Other suitable base analogues are known to those of skill in the art, such as, for example, those presented elsewhere herein.

Also presented herein is a kit for amplifying a nucleic acid sample, the kit comprising a set of $T_m$-normalized amplification primers, wherein each primer of the set of $T_m$-normalized amplification primers comprises one or more base analogues that normalize the Tm of each primer to the Tm of other amplification primers in the kit. In certain aspects, the kit further comprises a set of instructions for combining the set of amplification primers with a nucleic acid library and amplifying the nucleic acid library. In certain aspects, the kit further comprises a DNA polymerase. In certain aspects, the set of $T_m$-normalized amplification primers is a mixture of primers.

Chimeric Primers

Another novel approach to reducing bias during random primer amplification is to utilize chimeric primers with a random 3' priming portion and a 5' constant sequence. Accordingly, presented herein is a method of creating a nucleic acid library from a nucleic acid sample, the method comprising: a) amplifying a nucleic acid sample with a set of random amplification primers, wherein each primer comprises a random 3' portion and a constant 5' priming portion, thereby producing amplification products, and wherein each amplification product comprises the constant 5' priming portion; b) circularizing the amplification products; and c) amplifying the circularized amplification products using primers which hybridize to the constant 5' priming portion. In certain aspects, the amplifying in step c) comprises performing multiple displacement amplification. In certain aspects, the set of random amplification primers is a mixture of primers.

An example of how this method can be utilized to generate a nucleic acid library with greater uniformity and reduced bias is presented below in Example 8.

In order to eliminate or reduce hairpin formation, the chimeric primers presented herein can optionally include a non-natural base between the random 3' portion and the constant 5' priming portion. It will be appreciated that any suitable non-natural base that serves to reduce or eliminate hairpin formation can be used. For example, in certain typical embodiments, the non-natural base is isoC.

Also presented herein is a kit for amplifying a nucleic acid sample, the kit comprising a set of random amplification primers comprising a random 3' portion and a constant 5' priming portion. In certain aspects, the kit further comprises a set of instructions for combining the set of amplification primers with a nucleic acid library and amplifying the nucleic acid library. In certain aspects, the kit further comprises a DNA polymerase. In certain aspects, the set of random amplification primers is a mixture of primers.

Random RNA Primers

Presented herein is the discovery that primer-primer extension artifacts can be reduced or minimized by employing non-interacting random primers. As used herein, the term non-interacting refers to primers designed so as to not hybridize with other primers during normal amplification conditions. Any type of non-interacting primers can be utilized in order to reduce primer-primer extension artifacts normally associated with random primer amplification. Accordingly, one approach is to use random primers that comprise RNA in at least the 3' portion of the primer. Thus, presented herein is a method of creating a nucleic acid library from a nucleic acid sample, the method comprising: a) amplifying a nucleic acid sample with a set of random amplification primers, wherein each primer comprises a random 3' portion and a constant 5' priming portion, and wherein the random 3' portion comprises RNA, thereby producing amplification products, wherein each amplification product comprises the constant 5' priming portion. In certain aspects, the set of random amplification primers is a mixture of primers. In certain aspects, the method further comprises: b) circularizing the amplification products; and c) amplifying the circularized amplification products using primers which hybridize to the constant 5' priming portion. In certain aspects, the amplifying in step c) comprises performing multiple displacement amplification.

Figure 7:
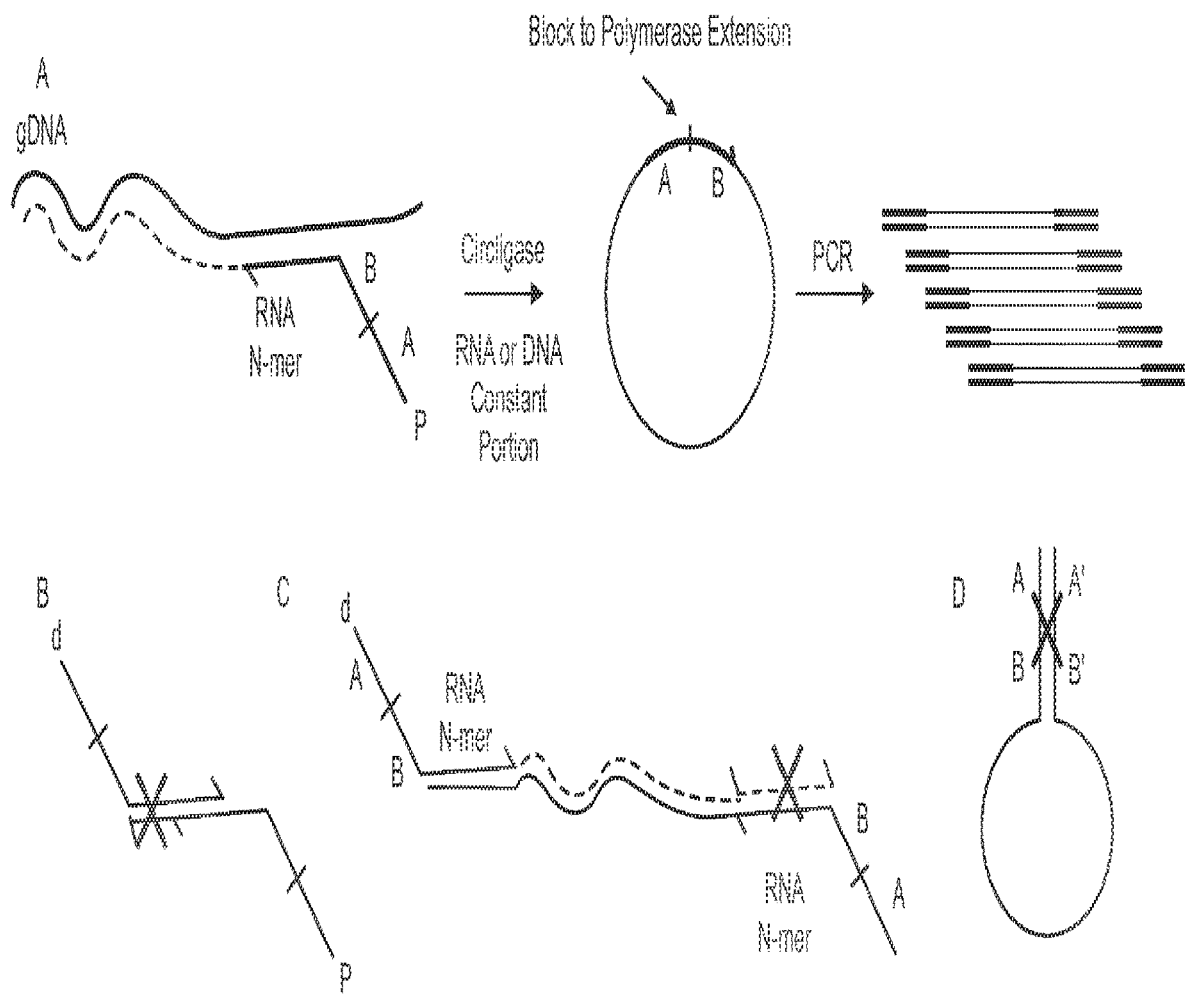
FIGS. 7A-D are diagrams setting forth an example of amplification of genomic DNA using random primers containing RNA.

An example of one use of this method is presented below in Example 9 and in FIG. 7.

Also presented herein is a kit for amplifying a nucleic acid sample, the kit comprising a set of random amplification primers, the primers comprising a random 3' portion and a constant 5' priming portion, wherein the random 3' portion comprises RNA. In certain aspects, the kit further comprises a set of instructions for combining the set of amplification primers with a nucleic acid library and amplifying the nucleic acid library. In certain aspects, the kit further comprises a DNA polymerase. In certain aspects, the set of random amplification primers is a mixture of primers.

Random DNA Primers with 2-Thio dT or 2-Amino-dA

Another approach to prevent primer-primer extension artifacts is to use random DNA primers that comprise 2-thio-dT and 2-amino-dA in at least the 3' portion of the primer. Thus, presented herein is a method of creating a nucleic acid library from a nucleic acid sample, the method comprising: amplifying a nucleic acid sample with a set of random amplification primers, wherein each primer comprises a random 3' portion and a constant 5' priming portion, and wherein the random 3' portion comprises at least one non-natural base selected from the group consisting of:

2-thio-dT and 2-amino-dA, thereby producing amplification products, wherein each amplification product comprises the constant 5' priming portion. In certain aspects, the set of random amplification primers is a mixture of primers. Incorporation of 2-thio-dT and 2-amino-dA into oligonucleotides can be performed according to any of a number of ways known in the art, as exemplified by Kutyavin et al. (1996) Biochemistry, 35:11170-11176, the disclosure of which is incorporated herein by reference in its entirety.

In certain aspects, the method further comprises: b) circularizing the amplification products; and c) amplifying the circular amplification products using primers that hybridize to the constant 5' priming portion. In certain aspects, the amplifying in step c) comprises performing multiple displacement amplification.

Also presented herein is a kit for amplifying a nucleic acid sample, the kit comprising random amplification primers, the primers comprising a random 3' portion and a constant 5' priming portion, wherein the random 3' portion comprises at least one non-natural base selected from the group consisting of: 2-thio-dT and 2-amino-dA. In certain aspects, the kit further comprises a set of instructions for combining the set of amplification primers with a nucleic acid library and amplifying the nucleic acid library. In certain aspects, the kit further comprises a DNA polymerase. In certain aspects, the set of random amplification primers is a mixture of primers.

Example 1

Whole Genome Amplification Using Multiple Displacement Amplification Including Locus Specific Primers Genomic DNA samples were obtained from Coriell Cell Repositories (Camden, N.J.). Genomic DNA concentrations were measured with the TaqMan RNase P Detection Reagents Kit and TaqMan Universal PCR Master Mix (Life Technologies, Foster City, Calif.) and Quant-iT PicoGreen dsDNA Reagent (Life Technologies, Foster City, Calif.).

The genomic DNA was diluted to various dilutions ranging from haploid copy numbers of 0.1n to 2n per 3 μl water. 3 μl of the diluted genomic DNA was aliquoted into multiple tubes. To each tube, 3 μl of Qiagen REPLI-g UltraFast D2 buffer was added followed by 10 minute incubation at 4° C. (Qiagen, Valencia, Calif.). 3 μl of REPLI-g UltraFast Stop Solution was added followed by the addition of 33 μl of Mastermix. The Mastermix contained 30 μl REPLI-g UltraFast Reaction Buffer, 41 REPLI-g UltraFast DNA Polymerase, and optionally 1 μl of 9-mer pool containing locus specific oligonucleotides designed specifically for the human genome (for a final concentration of 0.03 μM per oligo). The Mastermix contains exonuclease-resistant random hexamers, in a concentration so that the final concentration in the reaction mixture was 50 μM hexamer. The reactions were incubated for 90 minutes at 30° C. followed by heat-inactivation for 3 minutes at 65° C. The Multiple Displacement Amplification (MDA) products were purified using DNA Clean & Concentrator-5 spin columns (Zymo Research, Irvine, Calif.) according to the manufacturer's protocol and eluted in 12 μl water. DNA concentrations of the amplified products were determined with Quant-iT™ PicoGreen dsDNA Reagent (Life Technologies, Foster City, Calif.).

Example 2

SNP Detection Using Genomic DNA Amplified Using Locus Specific Primers

A single nucleotide polymorphism (SNP) site, shown in FIG. 1 as "A/G" is located in a DNA locus illustrated by thin lines. Primers, shown in FIG. 1 as arrows, are designed and annealed to DNA on both sides of the SNP site. Whole genome amplification (WGA) is initiated as described in Example 1. Performing WGA using locus specific primers generates a number of amplification products of varying lengths, shown in FIG. 1. These amplification products are further amplified during WGA using locus specific primers as well as random primers presented in the reaction mixture.

Example 3

Use of Locus Specific Primers to Increase Signal Intensity of Genotyping Assay

Figure 2:
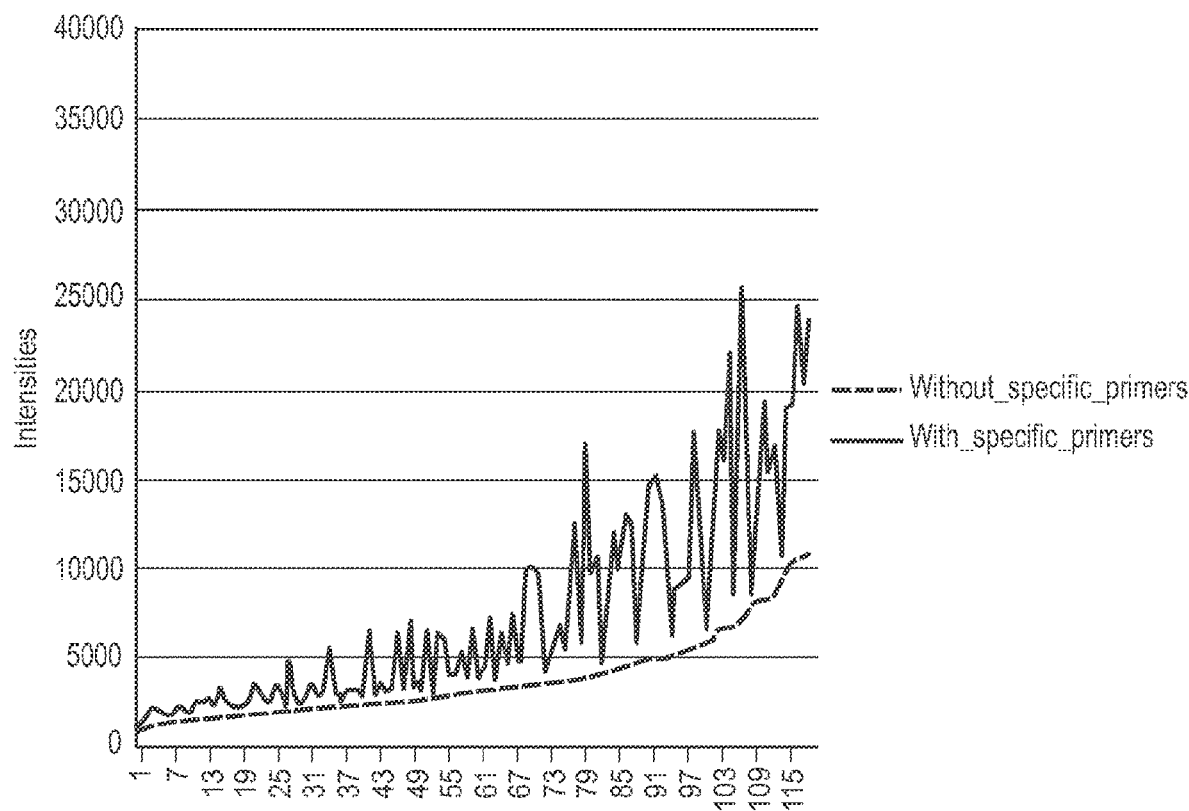
FIG. 2 is a graph showing signal intensity of 120 probes on a genotyping bead array for DNA samples amplified with and without locus specific primers designed for the regions surrounding the sequences of the capture probes. An obvious increase in signal intensity, averaging 1.8 fold, is shown for the DNA sample amplified with the set of locus specific primers.

Whole genome amplification (WGA) was initiated as described in Example 1, either with or without the addition of locus specific primers designed for the regions surrounding the sequences of 120 capture probes. Amplified products were then analyzed using an INFINIUM™ genotyping bead array (Illumina, San Diego, Calif.). The signal intensities of the 120 probes were plotted, and are set forth in FIG. 2. As shown in FIG. 2, an obvious increase in signal intensity, averaging at 1.8 fold was observed for the DNA sample amplified using the set of locus specific primers.

Example 4

SNP Detection Using Genomic DNA Amplified Using Locus Specific Primers

Figure 3:
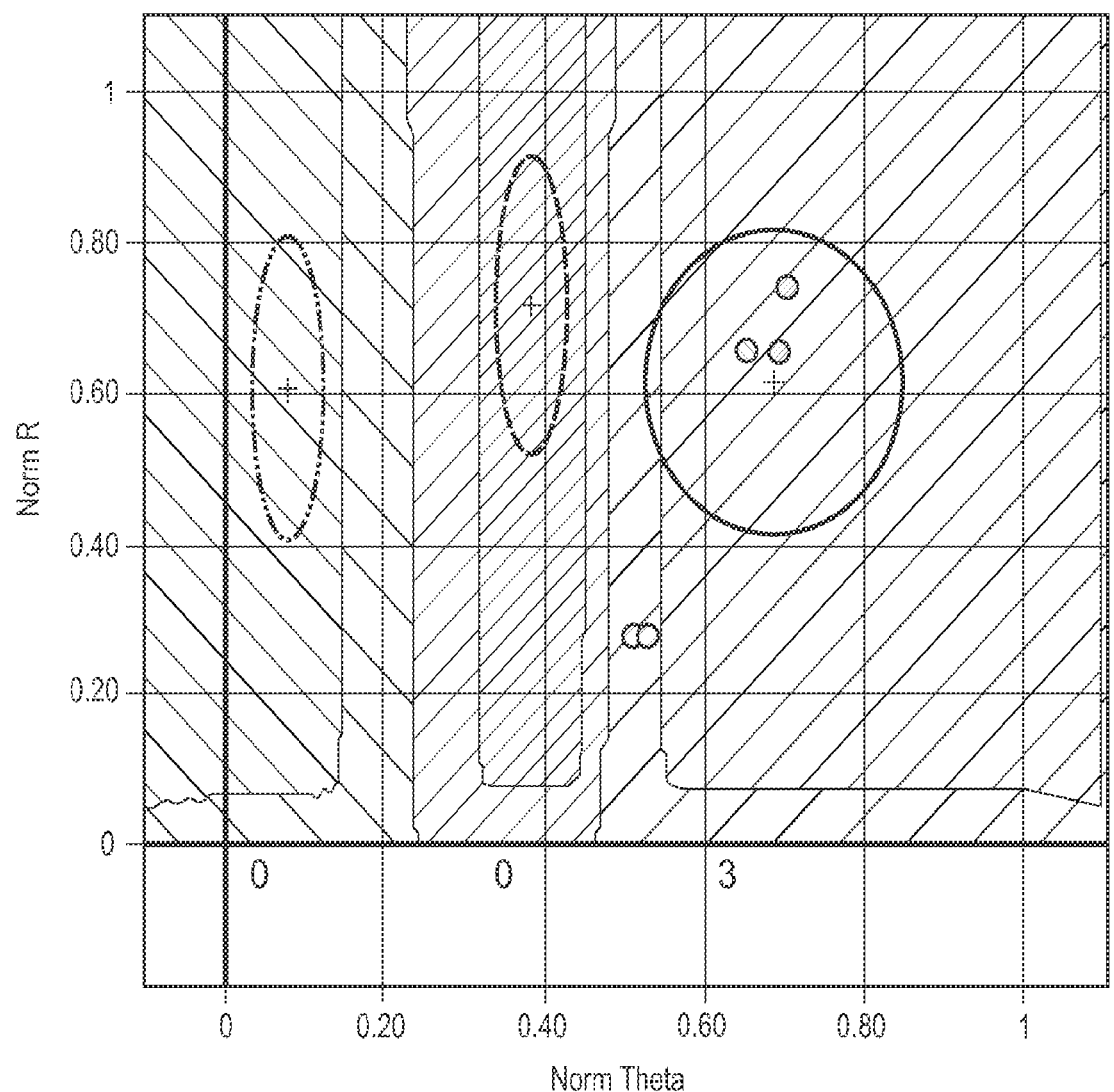
FIG. 3 is a SNP graph for a selected SNP site for two replicates of a DNA sample amplified with or without a set of locus specific primers designed for the region surrounding the sequence of the SNP.

Whole genome amplification (WGA) was initiated as described in Example 1, either with or without the addition of locus specific primers designed to the region surrounding a SNP of interest. A SNP analysis for a selected SNP site was performed for two replicates of the DNA sample amplified in the WGA reaction. A graph of the SNP analysis is shown in FIG. 3. FIG. 3 shows that the selected SNP was successfully genotyped in the DNA sample amplified in the presence of locus specific primers.

Example 5

Use of Locus Specific Primers in Single Cell Genotyping Assay

Whole genome amplification (WGA) was initiated on a DNA sample from a single cell, using the parameters described in Example 1, either with or without the addition of approximately 6,000 specific 9-mers which are highly represented in the human genome. With the addition of these humanized 9-mer primers, more robust amplification was achieved, as described below.

Figure 4:
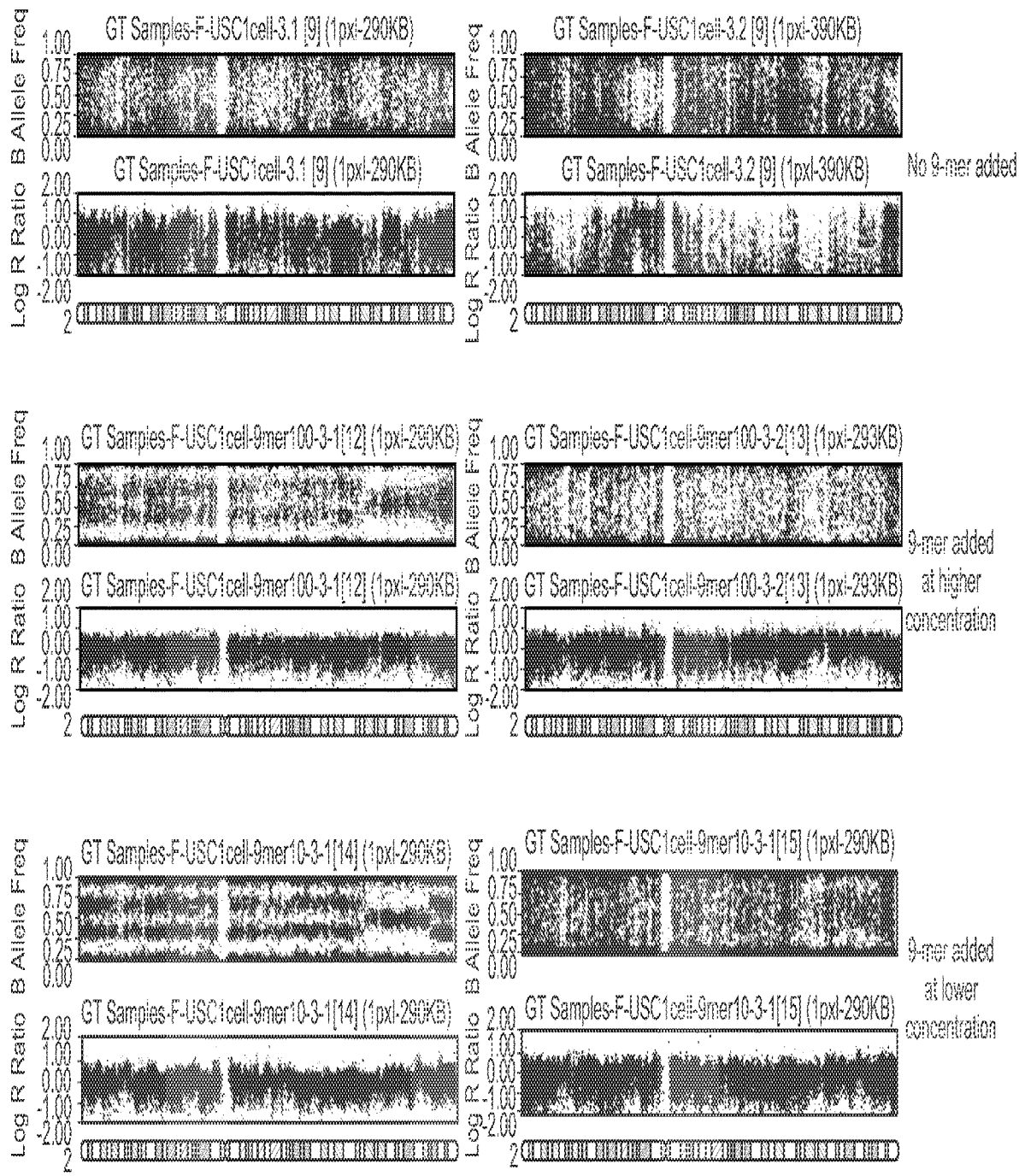
FIG. 4 shows signal intensity across human chromosome 2 for samples amplified with or without locus specific 9-mers at high or low concentration.

A typical result is shown in FIG. 4, which shows signal intensity across human chromosome 2. As shown in FIG. 4, amplification reactions that included the 9-mer primers resulted in a more robust, homogeneous amplification across the whole chromosome which greatly reduced bias across the amplified chromosome, when compared to amplification without the 9-mers. Nucleotide sequencing call rate and call accuracy were also significantly improved in amplification reactions that included the 9-mers, compared to amplification without the 9-mers.

Example 6

Use of AT-Rich Primers and Primers with AT-Rich 5' Tails in Genomic Amplification Four different sets of primers are designed and synthesized as set forth in the table below. In the table, the first two sets have 5' AT tails. The second three sets have biased base degeneracy. W=(A/T). The base composition format is specified as [A-C-G-T]. An equimolar mixture is specified as [25-25-25-25].

| Mixture | Sequence (5'-3') |
|---|---|
| N9-3AT | [W] [W] [W] [25-25-25-25] [25-25-25-25] [25-25-25-25] [25-25-25-25] [25-25-25-25] [25-25-25-25] [25-25-25-25] [25-25-25-25] [N] |
| N9-6AT | [W] [W] [W] [W] [W] [W] [25-25-25-25] [25-25-25-25] [25-25-25-25] [25-25-25-25] [25-25-25-25] [25-25-25-25] [25-25-25-25] [25-25-25-25] [N] |
| N9-AT-rich | [35-15-15-35] [35-15-15-35] [35-15-15-35] [35-15-15-35] [35-15-15-35] [35-15-15-35] [35-15-15-35] [35-15-15-35] [N] |
| N12-AT-rich | [35-15-15-35] [35-15-15-35] [35-15-15-35] [35-15-15-35] [35-15-15-35] [35-15-15-35] [35-15-15-35] [35-15-15-35] [35-15-15-35] [35-15-15-35] [35-15-15-35] [N] |
| N15-AT-rich | [35-15-15-35] [35-15-15-35] [35-15-15-35] [35-15-15-35] [35-15-15-35] [35-15-15-35] [35-15-15-35] [35-15-15-35] [35-15-15-35] [35-15-15-35] [35-15-15-35] [35-15-15-35] [35-15-15-35] [35-15-15-35] [N] |

Random primer amplification (RPA) using an AT-rich random 9-mer was evaluated by amplifying Coriell DNA using either standard composition 9-mer ([25-25-25-25]) vs. AT-rich 9-mer ([35-15-15-35]). The amplified product was run in a standard Infinium™ genotyping assay and the effect of the raw signal intensities as a function of GC content of the probe was plotted. The results are set forth in FIG. 8.

Figure 8:
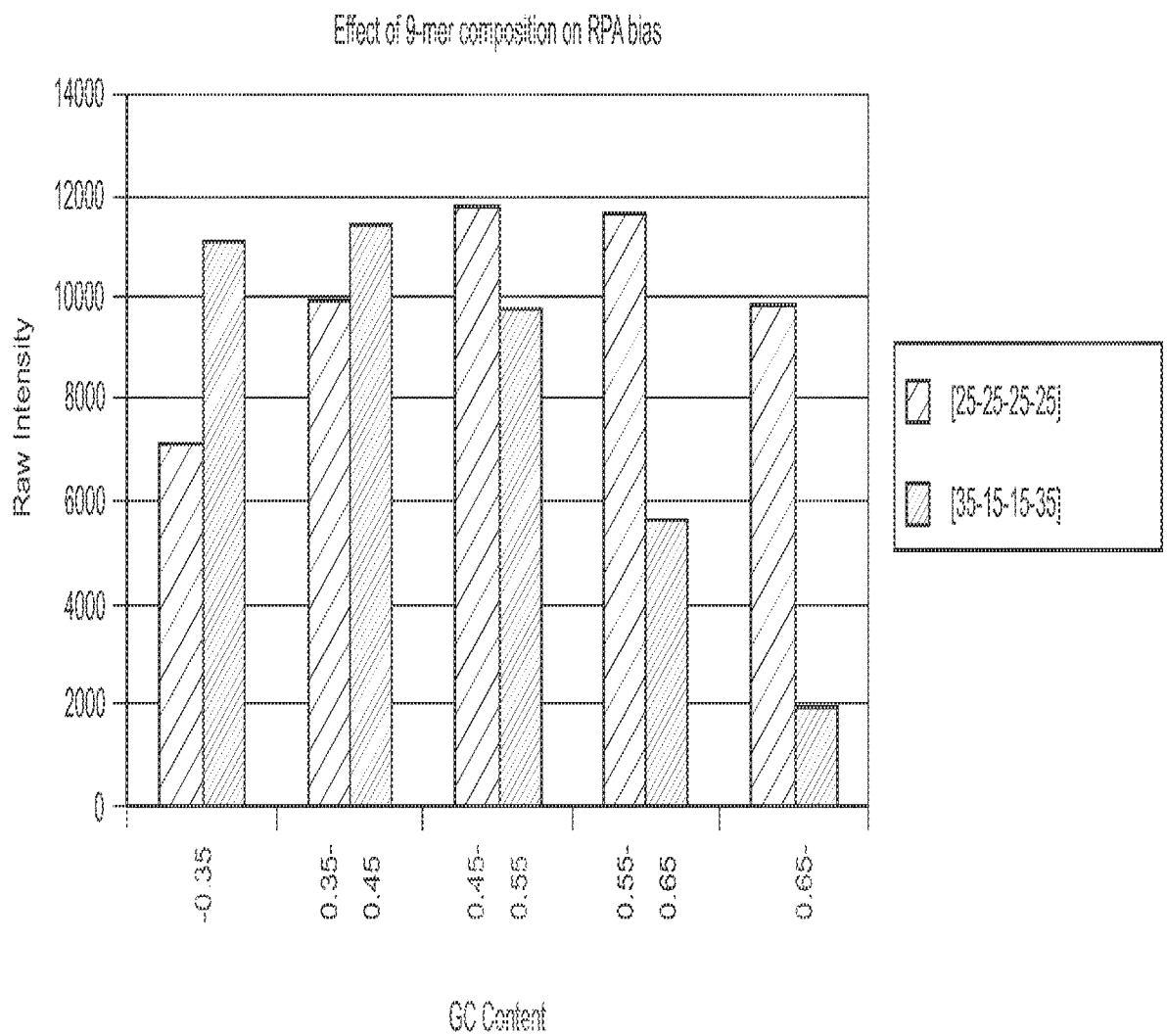
FIG. 8 is a bar graph showing the effect of 9-mer composition on Random Primer Amplification (RPA) bias.

As shown in FIG. 8, the AT-biased 9-mer (35-15-15-35) clearly increased the intensity of the AT-rich probes and decreased the intensity of the GC-rich probes relative to the standard.

Example 7

Normalization of Overall™ of a Primer Mixture with Degenerate 5' Tails

Synthesis of a set of fully degenerate 6-mers (N) was designed. Likewise, a separate set of fully degenerate 6-mers was designed to include an additional 5' tail proportional in length to the A/T content of the 6-mer. The overall $T_m$ of each primer mix was calculated. The results are set forth in FIG. 5. As shown in FIG. 5, addition of tails to the 6-mer mix results in an increase in the overall $T_m$, and a decrease in the standard deviation of the overall Tm for the mix.

The same concept is applied to a random 7-mer. A set of fully degenerate 7-mers was designed to include variable-length 5-tails that are proportional in length to the A/T content of the 7-mer. The full set of 7-mers is set forth in the table below.

| | | | | | |
|---|---|---|---|---|---|
| NNNWWWWWWW | NNWWSSWWW | NNWSSWWWW | NNASSASSS | NNSSWWWWW | NSSSSWWW |
| NNNWWWWWWS | NNWWSSWWWS | NNSWWSWWS | NNSSWWWWS | NSSSSWWS | NSSSSWWS |
| NNNWWWWWSW | NNWWSSWSW | NNWSSWWSW | NNSWWSWSW | NNSSWWWSW | NSSSSWSW |
| NNWWWWWSS | NWWSSWSS | NWSWWSS | NSWWSKSS | NSSWWWSS | SSSSWSS |
| NNNWWWWSWW | NNWWSSSWW | NNWSSWSWW | NNSWWSSWW | NNSSWWSWW | NSSSSSWW |
| NNWWWWSWS | NWWSSSWS | NWSSWSWS | NSWWSSWS | NSSWWSWS | SSSSSWS |
| NNWWWWSSW | NWWSSSWS | NWSSWSSW | NSWWSSSW | NSSWWSSW | SSSSSSW |
| NNWWWWSSS | NWWSSSSS | NWSSWSSS | NSWWSSSS | NSSWWSSS | SSSSSSS |
| NNNWWSWWW | NNNWSWWWWW | NNWSSSWWW | NNSWSVWWW | NNSSWSWWW | |
| NNWWWSWWS | NNWSWWWWS | NWSSSWWS | NNSWSWWWS | NSSWSWWS | |
| NNWWW8WSW | NNWSWWWSW | NWSSSWSW | NWSWSWWSW | NSSWSWSW | |
| NNWWWSWSS | WNWSWWWSS | NWSSSWSS | NSW8WWSS | NSSWSWSS | |
| NNWWWSSWW | NNWSWWSWW | NWSSSSWW | NNSWSWSWW | NSSWSWW | |
| NNWWWSSWS | NNWSWWSWS | NWSSSSWS | NSWSWSWS | NSSWSSWS | |
| NNWWWSSSW | NNWSWWSSW | NWSSSSSW | NSWSWSSW | NSSWSSSW | |
| NWWWSSSS | NWSWWSSS | WSSSSSS | NSWSWSSS | SSWSSSS | |
| NNNWWSWWWW | NNWSWSWWW | NNWSWWWWWW | NNSWSSWWW | NNSSSWWWW | |
| NNWWSWWWS | NNWSWSWWS | NNSWWWWWS | NSWSSWWS | NSSSWWWS | |

-continued

| | | | | |
|---|---|---|---|---|
| NNWWSWWSW | NNWSWSWSW | NNSWWWSW | NSWSSWSW | NSSSWWSW |
| NNWWSWWSS | NWSWSWSS | NNSWWWSS | NSWSSWSS | NSSSWWSS |
| NNWWSWSWW | NNWSWSSWW | NNSWWWSWW | NSWSSSWW | NSSSWSWW |
| NWWWSWSWS | NWSWSSWS | NNSWWW8WS | NSNSMWS | NSSSWSWS |
| WWWSWSSW | NWSWSSSW | NNSWWWSSW | NSWSSSSW | NSSSWSSW |
| NWWSWSSS | NWSWSSSS | NSWWWSSS | SWSSSSS | SSSWSSS |

Example 8

Use of Chimeric Primers to Reduce Amplification Bias

This example describes the use of a chimeric random-mer primer which comprises a constant sequence for amplification of nucleic acid. As described below, the random portion of the primer is used for priming from the source nucleic acid, genomic DNA in this case. The constant portion is then used for unbiased exponential amplification of the sequences amplified using the random primer.

Figure 6:
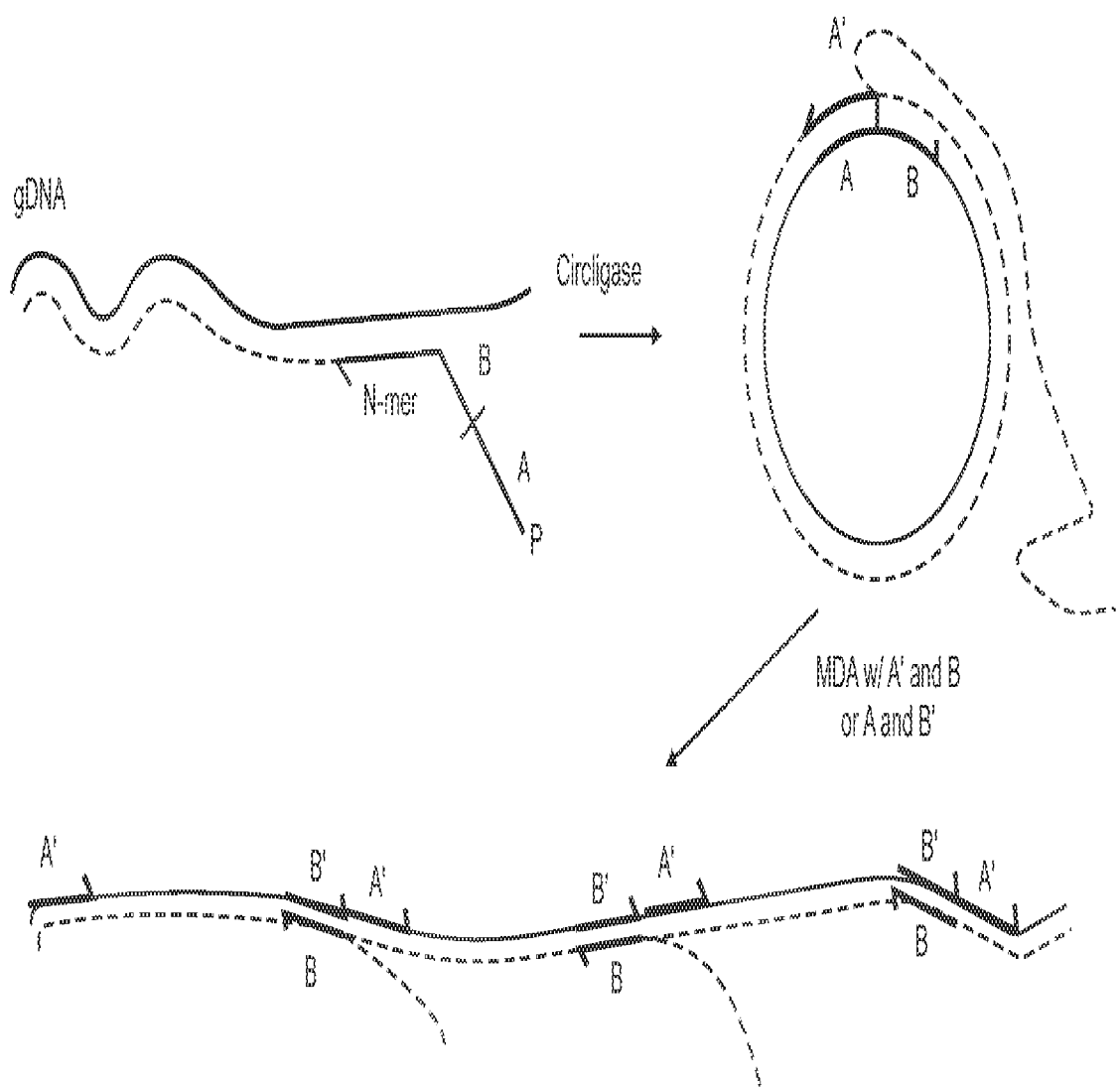
FIG. 6 is a diagram setting forth an example of amplification of genomic DNA using chimeric primers.

As illustrated in FIG. 6, amplification from genomic DNA (gDNA) is initially primed using the random portion of random-constant primer chimeric primer containing 3' random sequence and 5' constant sequence (A-B portion). After limited initial random priming, the product is circularized with CircLigase™, and then primed in a multiple displacement amplification (MDA) reaction with the constant sequence primer pairs A' and B, or A and B'. This leads to unbiased exponential amplification of the circular DNA. In typical embodiments illustrated in FIG. 6, the constant sequence (A-B) is rare in the genome being amplified. The table below sets forth an example of chimeric sequences used in this process, where cA and cB indicate complementary primers for the A and B constant sequences of the chimeric primer AB-N9 (Table discloses SEQ ID NOS 1-5, respectively, in order of appearance).

| A | 5'-TCGCGAGTTAA |
|---|---|
| C | 5'-ATTGCGAACGA |
| cA | 5'-TTAACTCGCGA |
| cB | 5'-TCGTTCGCAAT |
| AB-N9 | 5'-TCGCGAGTTAAATTGCGAACGANNNNNNNNN |

In a further example, the chimeric primers comprise a non-natural base (i.e., isoC) between the constant portion and the random portion of the primer. During the MDA step, inclusion of isoC and isoG along with other nucleotides enables its amplification.

Example 9

Use of RNA-DNA Chimeric Primers to Reduce Primer-Primer Extension Artifacts

This example describes RNA-based random primer amplification to reduce primer-primer extension artifacts. As shown in FIG. 7, random priming with RNA containing primers enables efficient circularization by CircLigase™ (FIG. 7A). Using RNA n-mer primers (RNA-DNA chimeric primers) will not support RNA primer dimer formation (FIG. 7B), but does support RNA on DNA extension. It also enables the RNA random n-mer portion to be cleaved off and eliminated from subsequent library generation steps. Finally, when using a primer containing a constant portion and a random portion, a RNA primer prevents formation of RPA products that can form "dumbbells" (FIGS. 7C and D) which can inhibit circularization by CircLigase™ shown in FIG. 7A. This is because DNA amplification reactions cannot prime on RNA except using a polymerase with reverse transcriptase activity.

Example 10

Genotyping of DNA Amplified from Direct Cell Lysates of 1 Cell, 5 Cells and 25 Cells Whole genome amplification was performed using either (1) standard MDA (with all random 6-mers), or standard random 6-mers plus enhanced primer pools, corresponding to the top 3,000 highly represented 9-mer sequences in the human genome, at (2) 40 PM or (3) 400 PM concentrations, respectively. Inclusion of sequence specific 9-mers in the reaction mix improved amplification across all loci that were genotyped.

What is claimed is:

1. A method of creating a nucleic acid library with reduced amplification bias from a nucleic acid sample comprising genomic DNA, the method comprising:
   a) providing a set of amplification primers to the nucleic acid sample comprising:
   (i) a plurality of random primers comprising primers selected from the group consisting of:
      (A) a set of variable-length random amplification primers, wherein each primer comprises a random 3' portion and a degenerate 5' tail that is proportional in length to the A/T content of the random 3' portion of the primer,
      (B) a first set of random amplification primers, wherein each primer comprises a random 3' portion that comprises RNA and a constant 5' priming portion, and
      (C) a second set of random amplification primers, wherein each primer comprises a random 3' portion and a constant 5' priming portion, wherein the random 3' portion comprises at least one non-natural base selected from the group consisting of 2-thio-dT and 2-amino-dA;
   (ii) a plurality of locus specific primers configured to amplify at least 100 predetermined genomic regions of the nucleic acids of the nucleic acid sample; and
   (iii) a plurality of blocked primers complementary to regions of a genome comprising repetitive sequences;
   wherein each plurality in the set of amplification primers is a mixture of primers; and
   b) amplifying the nucleic acid sample using the set of amplification primers thereby creating a nucleic acid library, wherein the amplifying provides more homogeneous amplification of the nucleic acid sample as compared to amplifying in the absence of the plurality of locus specific primers.

2. The method of claim 1, wherein the random primers are from 5 to 18 nucleotides in length.

3. The method of claim 2, wherein the random primers are 9 nucleotides in length.

4. The method of claim 1, wherein the plurality of blocked primers comprise a 3' blocking group.

5. The method of claim 1, wherein the plurality of blocked primers lack a 3' OH.

6. The method of claim 1, wherein said locus specific primers comprise sequences specific to one or more repetitive regions of a genome.

7. The method of claim 1, wherein said locus specific primers comprise exonuclease-resistant primers, and wherein the amplifying comprises amplifying in the presence of a polymerase with exonuclease activity.

8. The method of claim 1, wherein said plurality of random primers are in greater abundance compared to said plurality of locus specific primers.

9. The method of claim 1, wherein the amplification primers comprise a set of Tm-normalized primers, wherein said primer set of Tm-normalized amplification primers comprises one or more base analogs selected from the group consisting of 2-thio-dT, 2-amino-dA, N4-Et-dC, and 7-deaza-G.

10. The method of claim 1, wherein the plurality of random primers comprise primers selected from the group consisting of:
an AT-rich set of random amplification primers;
a set of random amplification primers comprising AT-rich 5' tails;
the set of variable-length random amplification primers, wherein each primer comprises a random 3' portion and a degenerate 5' tail that is proportional in length to the A/T content of the random 3' portion of the primer;
a set of $T_m$-normalized amplification primers, wherein each primer of said set comprises one or more base analogs that normalize the $T_m$ of each primer to the $T_m$ of other primers in the set of primers;
a set of random amplification primers, wherein each primer comprises a random 3' portion and a constant 5' priming portion;
the first set of random amplification primers, wherein each primer comprises a random 3' portion that comprises RNA and a constant 5' priming portion;
the second set of random amplification primers, wherein each primer comprises a random 3' portion and a constant 5' priming portion, wherein the random 3' portion comprises at least one non-natural base selected from the group consisting of 2-thio-dT and 2-amino-dA; and
any combination of the foregoing sets of primers.

11. The method of claim 1, wherein the plurality of locus specific primers are configured to hybridize to non-repetitive sequences in the human genome.

12. The method of claim 1, wherein the plurality of locus specific primers is configured to amplify at least 1000 predetermined genomic regions of the nucleic acid sample.

13. The method of claim 1, wherein the nucleic acid sample is a single cell.

14. The method of claim 1, wherein the plurality of locus specific primers is configured to amplify sequences that are distributed across the genomic DNA.

15. The method of claim 1, wherein the at least 100 predetermined genomic regions comprise regions distributed evenly along the length of at least a portion of a genome.

16. The method of claim 1, wherein the concentration of a first locus specific primer of the plurality of locus specific primers is different from the concentration of a second locus specific primer of the plurality of locus specific primers.

17. The method of claim 1, wherein the plurality of random primers comprises the set of variable-length random amplification primers, wherein each primer comprises a random 3' portion and a degenerate 5' tail that is proportional in length to the A/T content of the random 3' portion of the primer.

18. The method of claim 1, wherein the at least 100 predetermined genomic regions comprise single nucleotide polymorphic (SNP) sites.

* * * * *

UNITED STATES PATENT AND TRADEMARK OFFICE
CERTIFICATE OF CORRECTION

PATENT NO. : 10,870,099 B2
APPLICATION NO. : 14/416563
DATED : December 22, 2020
INVENTOR(S) : Jian-Bing Fan et al.

Page 1 of 2

It is certified that error appears in the above-identified patent and that said Letters Patent is hereby corrected as shown below:

On the Title Page

On page 2, in Column 1, item (56), Other Publications, Line 8, delete "WatsonCrick" and insert --Watson-Crick--.

On page 2, in Column 1, item (56), Other Publications, Line 27, delete "phosphoamidate" and insert --phosphoramidate--.

On page 2, in Column 2, item (56), Other Publications, Line 1, delete "Phosporamidate" and insert --Phosphoramidate--.

On page 2, in Column 2, item (56), Other Publications, Line 3, delete "oliodeoxynucleotide" and insert --oligodeoxynucleotide--.

On page 2, in Column 2, item (56), Other Publications, Line 8, delete "polyumerases" and insert --polymerases--.

On page 2, in Column 2, item (56), Other Publications, Line 33, delete "Miscrosatellite" and insert --Microsatellite--.

In the Specification

In Column 15, Line 7, delete "(1" and insert --(I--.

In Column 18, Line 38, delete "Saccharamoyces" and insert --Saccharomyces--.

In Column 18, Line 44, delete "Archae" and insert --Archaea--.

In Column 20, Line 64, delete "91986))" and insert --91986)--.

Signed and Sealed this
Ninth Day of March, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,870,099 B2

In Columns 20-21, Lines 67-1, delete "O-methylphophoroamidite" and insert --O-methylphosphoramidite--.

In Column 21, Line 9, delete "(1995);" and insert --(1995));--.

In Column 21, Line 36, delete "allcaryl," and insert --alkaryl,--.

In Column 21, Line 37, delete "arallcyl," and insert --aralkyl,--.

In Column 21, Line 37, delete "O-allcaryl" and insert --O-alkaryl--.

In Column 21, Line 39, delete "heterocycloallcyl," and insert --heterocycloalkyl,--.

In Column 21, Line 39, delete "heterocycloallcaryl," and insert --heterocycloalkaryl,--.

In Column 21, Lines 39-40, delete "aminoallcylamino, polyallcylamino" and insert --aminoallylamino, polyalkylamino--.

In Column 21, Line 54, delete "xathanine" and insert --xanthine--.

In Column 21, Line 55, delete "hypoxathanine" and insert --hypoxanthine--.

In Column 21, Line 58, delete "thioLiracil" and insert --thiouracil--.

In Column 23, Line 28, delete "T" and insert --$T_m$--.

In Column 29, Line 45, delete "41" and insert --2 μl--.

In Column 31, Line 29 (approx.), delete "(N)" and insert --(NNNNNN)--.

In Column 33, Line 43 (approx.), delete "C" and insert --B--.

In the Claims

In Column 37, Line 24 (approx.), Claim 9, delete "Tm" and insert --$T_m$--.

In Column 37, Line 25 (approx.), Claim 9, delete "Tm" and insert --$T_m$--.